US009072523B2

(12) United States Patent
Houser et al.

(10) Patent No.: US 9,072,523 B2
(45) Date of Patent: Jul. 7, 2015

(54) MEDICAL DEVICE WITH FEATURE FOR STERILE ACCEPTANCE OF NON-STERILE REUSABLE COMPONENT

(75) Inventors: Kevin L. Houser, Springboro, OH (US); Foster B. Stulen, Mason, OH (US); William D. Dannaher, Cincinnati, OH (US); Bret W. Smith, Kings Mills, OH (US); David N. Plescia, Cincinnati, OH (US); Michael J. Stokes, Cincinnati, OH (US); Sora Rhee, Cincinnati, OH (US); Timothy G. Dietz, Terrace Park, OH (US); Kevin D. Felder, Cincinnati, OH (US); Christopher B. Anderson, Oak Grove, MN (US); Jeffrey L. Aldridge, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1032 days.

(21) Appl. No.: 13/151,512

(22) Filed: Jun. 2, 2011

(65) Prior Publication Data

US 2012/0110810 A1 May 10, 2012

Related U.S. Application Data

(60) Provisional application No. 61/410,603, filed on Nov. 5, 2010, provisional application No. 61/487,846, filed on May 19, 2011.

(51) Int. Cl.
*A61B 19/02* (2006.01)
*A61B 18/14* (2006.01)
(Continued)

(52) U.S. Cl.
CPC .............. *A61B 18/1442* (2013.01); *H01M 2/26* (2013.01); *H01M 2/10* (2013.01); *A61B 18/1206* (2013.01);
(Continued)

(58) Field of Classification Search
USPC ......... 29/271, 280, 281.5; 220/256.1, 257.51, 220/259.1, 259.2, 264, 254.5, 838, 254.3, 220/831, 236, 257.1, 257.2, 359.1, 359.2, 220/254.1; 206/438, 366; 128/830, 840
See application file for complete search history.

(56) References Cited

U.S. PATENT DOCUMENTS 1,754,806 A   4/1930   Stevenson
3,297,192 A * 1/1967   Swett ........................... 220/840
(Continued)

FOREIGN PATENT DOCUMENTS

DE   102008051866   10/2010
DE   102009013034   10/2010
(Continued)

OTHER PUBLICATIONS

European Communication dated Feb. 19, 2014 for Application No. EP 11781972.2.
(Continued)

*Primary Examiner* — Lee D Wilson
*Assistant Examiner* — Henry Hong
(74) *Attorney, Agent, or Firm* — Frost Brown Todd LLC

(57) ABSTRACT

An apparatus maintains the sterility of a medical device while providing for the insertion of an insertable component into the medical device. The apparatus includes a medical device having a housing sized to contain the insertable component, an active feature, a cap, and a hinge member. A container encases the medical device within a device recess, a cap recess, and a container cover. The insertable component may be inserted into the housing while limiting potential contact with the exterior of the medical device. An alternative assembly comprises an insertion assembly having a handle and the insertable component detachably attached thereto. The medical device comprises a housing, an active feature, and a flexible member. An insertion tube is insertable within the flexible member to limit contact when the insertable component is inserted into the housing. Yet another configuration includes a resiliently hinged door assembly releasable by a release button.

15 Claims, 21 Drawing Sheets

(51) Int. Cl.
*A61B 17/00* (2006.01)
*A61B 17/32* (2006.01)
*A61B 18/00* (2006.01)
*A61B 18/04* (2006.01)
*H02J 7/00* (2006.01)
*H01M 2/26* (2006.01)
*H01M 2/10* (2006.01)
*A61B 18/12* (2006.01)
*A61B 19/00* (2006.01)
*A61B 17/064* (2006.01)
*A61B 17/285* (2006.01)
*A61B 17/29* (2006.01)

(52) U.S. Cl.
CPC ............ *A61B 19/56* (2013.01); *Y10T 29/53913* (2015.01); *Y10T 29/49895* (2015.01); *Y10T 29/49005* (2015.01); *A61B 17/00234* (2013.01); *A61B 17/064* (2013.01); *A61B 17/285* (2013.01); *A61B 17/320068* (2013.01); *A61B 17/320092* (2013.01); *A61B 18/00* (2013.01); *A61B 18/04* (2013.01); *A61B 18/12* (2013.01); *A61B 18/1233* (2013.01); *A61B 18/14* (2013.01); *A61B 18/1445* (2013.01); *A61B 19/38* (2013.01); *A61B 2017/00084* (2013.01); *A61B 2017/00398* (2013.01); *A61B 2017/0046* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/2929* (2013.01); *A61B 2017/293* (2013.01); *A61B 2017/2931* (2013.01); *A61B 2017/2933* (2013.01); *A61B 2017/294* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2019/4815* (2013.01); *A61B 2019/4868* (2013.01); *A61B 2019/4873* (2013.01); *H02J 7/0045* (2013.01)

(56) References Cited

U.S. PATENT DOCUMENTS

| | | | |
|---|---|---|---|
| 3,419,198 A * | 12/1968 | Pettersen | 222/541.2 |
| 3,619,671 A | 11/1971 | Shoh | |
| 4,034,762 A | 7/1977 | Cosens et al. | |
| 4,057,220 A | 11/1977 | Kudlacek | |
| 4,535,773 A | 8/1985 | Yoon | |
| 4,641,076 A | 2/1987 | Linden et al. | |
| 4,662,068 A | 5/1987 | Polonsky | |
| 4,666,037 A * | 5/1987 | Weissman | 206/63.5 |
| 4,685,459 A | 8/1987 | Koch et al. | |
| 4,717,018 A * | 1/1988 | Sacherer et al. | 206/305 |
| 4,717,050 A * | 1/1988 | Wright | 222/482 |
| 4,721,097 A | 1/1988 | D'Amelio | |
| 4,768,969 A | 9/1988 | Bauer et al. | |
| 4,800,878 A | 1/1989 | Cartmell | |
| 4,844,259 A | 7/1989 | Glowczewskie, Jr. et al. | |
| 4,878,493 A | 11/1989 | Pasternak et al. | |
| 5,071,417 A | 12/1991 | Sinofsky | |
| 5,107,155 A | 4/1992 | Yamaguchi | |
| 5,144,771 A | 9/1992 | Miwa | |
| 5,169,733 A | 12/1992 | Savovic et al. | |
| 5,176,677 A | 1/1993 | Wuchinich | |
| 5,246,109 A | 9/1993 | Markle et al. | |
| 5,273,177 A * | 12/1993 | Campbell | 220/281 |
| 5,277,694 A | 1/1994 | Leysieffer et al. | |
| 5,308,358 A | 5/1994 | Bond et al. | |
| 5,322,055 A | 6/1994 | Davison | |
| 5,339,799 A | 8/1994 | Kami et al. | |
| 5,358,508 A | 10/1994 | Cobb et al. | |
| 5,361,902 A | 11/1994 | Abidin et al. | |
| 5,429,229 A * | 7/1995 | Chester et al. | 206/63.5 |
| 5,449,370 A | 9/1995 | Vaitekumas | |
| 5,454,378 A | 10/1995 | Palmer et al. | |
| 5,501,607 A * | 3/1996 | Yoshioka et al. | 439/142 |
| 5,507,297 A | 4/1996 | Slater et al. | |
| 5,561,881 A | 10/1996 | Klinger et al. | |
| 5,578,052 A | 11/1996 | Koros et al. | |
| 5,580,258 A * | 12/1996 | Wakata | 439/142 |
| 5,582,617 A | 12/1996 | Klieman et al. | |
| 5,590,778 A | 1/1997 | Dutchik | |
| 5,592,065 A | 1/1997 | Oglesbee et al. | |
| 5,597,531 A | 1/1997 | Liberti et al. | |
| 5,599,350 A | 2/1997 | Schulze et al. | |
| 5,630,420 A | 5/1997 | Vaitekunas | |
| 5,630,456 A | 5/1997 | Hugo et al. | |
| 5,690,222 A * | 11/1997 | Peters | 206/339 |
| 5,707,369 A | 1/1998 | Vaitekunas et al. | |
| 5,741,305 A | 4/1998 | Vincent et al. | |
| 5,776,155 A | 7/1998 | Beaupre et al. | |
| 5,800,336 A | 9/1998 | Ball et al. | |
| 5,817,128 A | 10/1998 | Storz | |
| 5,868,244 A | 2/1999 | Ivanov et al. | |
| 5,873,873 A | 2/1999 | Smith et al. | |
| 5,882,310 A | 3/1999 | Marian, Jr. | |
| 5,935,144 A | 8/1999 | Estabrook | |
| 5,938,633 A | 8/1999 | Beupre | |
| 5,944,737 A | 8/1999 | Tsonton et al. | |
| 5,951,575 A | 9/1999 | Bolduc et al. | |
| 5,980,510 A | 11/1999 | Tsonton et al. | |
| 5,997,531 A | 12/1999 | Loeb et al. | |
| 6,018,227 A | 1/2000 | Kumar et al. | |
| 6,051,010 A | 4/2000 | Dimatteo et al. | |
| 6,056,735 A | 5/2000 | Okada et al. | |
| 6,063,098 A | 5/2000 | Houser et al. | |
| 6,066,151 A | 5/2000 | Miyawaki et al. | |
| 6,083,191 A | 7/2000 | Rose | |
| 6,083,223 A | 7/2000 | Baker | |
| 6,099,537 A | 8/2000 | Sugai et al. | |
| 6,113,593 A | 9/2000 | Tu et al. | |
| 6,123,702 A | 9/2000 | Swanson et al. | |
| 6,165,191 A | 12/2000 | Shibata et al. | |
| 6,204,592 B1 | 3/2001 | Hur | |
| 6,214,023 B1 | 4/2001 | Whipple et al. | |
| 6,246,896 B1 | 6/2001 | Dumoulin et al. | |
| 6,248,238 B1 | 6/2001 | Burtin et al. | |
| 6,287,304 B1 | 9/2001 | Eggers et al. | |
| 6,325,811 B1 | 12/2001 | Messerly | |
| 6,339,368 B1 | 1/2002 | Leith | |
| 6,398,755 B1 | 6/2002 | Belef et al. | |
| 6,409,742 B1 | 6/2002 | Fulton, III et al. | |
| 6,500,176 B1 | 12/2002 | Truckai et al. | |
| 6,500,188 B2 | 12/2002 | Harper et al. | |
| 6,514,267 B2 | 2/2003 | Jewett | |
| 6,520,185 B1 | 2/2003 | Bommannan et al. | |
| 6,561,983 B2 | 5/2003 | Cronin et al. | |
| 6,609,414 B2 | 8/2003 | Mayer et al. | |
| 6,622,731 B2 | 9/2003 | Daniel et al. | |
| 6,623,500 B1 | 9/2003 | Cook et al. | |
| 6,626,901 B1 | 9/2003 | Treat et al. | |
| 6,647,281 B2 | 11/2003 | Morency | |
| 6,650,975 B2 | 11/2003 | Ruffner | |
| 6,656,177 B2 | 12/2003 | Truckai et al. | |
| 6,658,301 B2 | 12/2003 | Loeb et al. | |
| 6,666,875 B1 | 12/2003 | Sakurai et al. | |
| 6,717,193 B2 | 4/2004 | Olewine et al. | |
| 6,730,042 B2 | 5/2004 | Fulton et al. | |
| 6,758,855 B2 | 7/2004 | Fulton, III et al. | |
| 6,761,698 B2 | 7/2004 | Shibata et al. | |
| 6,761,701 B2 | 7/2004 | Cucin | |
| 6,783,524 B2 | 8/2004 | Anderson et al. | |
| 6,815,206 B2 | 11/2004 | Lin et al. | |
| 6,821,671 B2 | 11/2004 | Hinton et al. | |
| 6,838,862 B2 | 1/2005 | Luu | |
| 6,860,880 B2 | 3/2005 | Treat et al. | |
| 6,869,435 B2 | 3/2005 | Blake | |
| 6,923,807 B2 | 8/2005 | Ryan et al. | |

(56) References Cited

U.S. PATENT DOCUMENTS

| | | | |
|---|---|---|---|
| 6,982,696 B1 | 1/2006 | Shahoian |
| 7,031,155 B2 | 4/2006 | Sauciuc et al. |
| 7,077,853 B2 | 7/2006 | Kramer et al. |
| 7,083,589 B2 | 8/2006 | Banko et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |
| 7,364,061 B2 | 4/2008 | Swayze et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,563,142 B1 | 7/2009 | Wenger et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,717,312 B2 | 5/2010 | Beetel |
| 7,721,936 B2 | 5/2010 | Shelton, IV et al. |
| 7,738,971 B2 | 6/2010 | Swayze et al. |
| 7,766,910 B2 | 8/2010 | Hixson et al. |
| 7,766,929 B2 | 8/2010 | Masuda |
| 7,770,722 B2 * | 8/2010 | Donahoe et al. ............ 206/63.5 |
| 7,770,775 B2 | 8/2010 | Shelton et al. |
| 7,776,037 B2 | 8/2010 | Odom |
| 7,780,660 B2 | 8/2010 | Bourne et al. |
| 7,815,658 B2 | 10/2010 | Murakami |
| 7,845,537 B2 | 12/2010 | Shelton, IV et al. |
| 7,846,159 B2 | 12/2010 | Morrison et al. |
| 7,889,489 B2 | 2/2011 | Richardson et al. |
| 7,922,063 B2 | 4/2011 | Zemlok et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 8,038,025 B2 * | 10/2011 | Stark et al. ............... 220/254.3 |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Sanai et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 * | 8/2012 | Ramsey et al. ............ 220/254.3 |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,888 B2 | 10/2012 | Whitman |
| 8,298,253 B2 | 10/2012 | Charles |
| 8,301,262 B2 | 10/2012 | Mi et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,564,242 B2 | 10/2013 | Hansford et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0171522 A1 | 8/2005 | Christopherson |
| 2005/0256522 A1 | 11/2005 | Francischelli et al. |
| 2006/0030797 A1 | 2/2006 | Zhou et al. |
| 2006/0079829 A1 | 4/2006 | Fulton, III et al. |
| 2006/0079874 A1 * | 4/2006 | Faller et al. .................. 606/40 |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0068943 A1 * | 3/2007 | Ramsey et al. ............ 220/254.3 |
| 2007/0084742 A1 | 4/2007 | Miller et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0105750 A1 | 4/2009 | Price et al. |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0209979 A1 | 8/2009 | Yates et al. |
| 2009/0209990 A1 * | 8/2009 | Yates et al. .................. 606/169 |
| 2009/0240246 A1 | 9/2009 | Deville et al. |
| 2009/0253030 A1 | 10/2009 | Kooij |
| 2009/0264940 A1 | 10/2009 | Beale et al. |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |

(56) References Cited

U.S. PATENT DOCUMENTS

| | | |
|---|---|---|
| 2010/0069940 A1 | 3/2010 | Miller et al. |
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Lyell Kirby et al. |
| 2010/0211053 A1 | 8/2010 | Ross et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0058982 A1 | 3/2011 | Kaneko |
| 2011/0077514 A1 | 3/2011 | Ulric et al. |
| 2011/0087218 A1 | 4/2011 | Boudreaux et al. |
| 2011/0152901 A1 | 6/2011 | Woodruff et al. |
| 2011/0224668 A1 | 9/2011 | Johnson et al. |
| 2011/0247952 A1 | 10/2011 | Habach et al. |
| 2012/0179036 A1 | 7/2012 | Patrick et al. |
| 2012/0265230 A1 | 10/2012 | Laurent et al. |
| 2012/0283732 A1 | 11/2012 | Lam |
| 2012/0292367 A1 | 11/2012 | Morgan et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090530 A1 | 4/2013 | Ramamurthy et al. |
| 2013/0090552 A1 | 4/2013 | Ramamurthy et al. |
| 2013/0116690 A1 | 5/2013 | Unger et al. |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

International Preliminary Report on Patentability for Application No. PCT/US2011/059212 dated May 7, 2013.
International Preliminary Report on Patentability for Application No. PCT/US2011/059215 dated May 8, 2013.
International Preliminary Report on Patentability for Application No. PCT/US2011/059217 dated May 7, 2013.
International Preliminary Report on Patentability for Application No. PCT/US2011/059218 dated May 7, 2013.
International Preliminary Report on Patentability for Application No. PCT/US2011/059220 dated May 7, 2013.
International Preliminary Report on Patentability for Application No. PCT/US2011/059222 dated May 7, 2013.
International Preliminary Report on Patentability for Application No. PCT/US2011/059223 dated May 7, 2013.
International Preliminary Report on Patentability for Application No. PCT/US2011/059226 dated May 7, 2013.
International Preliminary Report on Patentability for Application No. PCT/US2011/059338 dated May 7, 2013.
International Preliminary Report on Patentability for Application No. PCT/US2011/059351 dated May 7, 2013.
International Preliminary Report on Patentability for Application No. PCT/US2011/059354 dated May 7, 2013.
International Preliminary Report on Patentability for Application No. PCT/US2011/059358 dated May 7, 2013.
International Preliminary Report on Patentability for Application No. PCT/US2011/059362 dated May 7, 2013.
International Preliminary Report on Patentability for Application No. PCT/US2011/059365 dated May 8, 2013.
International Preliminary Report on Patentability for Application No. PCT/US2011/059371 dated May 7, 2013.
International Preliminary Report on Patentability for Application No. PCT/US2011/059378 dated May 7, 2013.
International Preliminary Report on Patentability for Application No. PCT/US2011/059381 dated May 8, 2013.
Office Action Non-Final dated Mar. 28, 2014 for U.S. Appl. No. 13/151,471.
Office Action Non Final dated Mar. 18, 2014 for U.S. Appl. No. 13/151,498.
Office Action Non Final dated Jun. 18, 2014 for U.S. Appl. No. 13/151,503.
Office Action Final dated Jan. 29, 2014 for U.S. Appl. No. 13/151,509.
Office Action Non-Final dated Feb. 14, 2014 for U.S. Appl. No. 13/274,480.
Restriction Requirement dated Dec. 9, 2013 for U.S. Appl. No. 13/274,496.
Office Action Non-Final dated Feb. 6, 2014 for U.S. Appl. No. 13/274,496.
Office Action Final dated May 15, 2014 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
Office Action Final dated Jun. 12, 2014 for U.S. Appl. No. 13/274,516.
Office Action Non-Final dated Jan. 6, 2014 for U.S. Appl. No. 13/275,514.
Office Action Final dated Feb. 28, 2014 for U.S. Appl. No. 13/275,547.
Office Action Final dated Mar. 21, 2014 for U.S. Appl. No. 13/276,673.

(56) References Cited

OTHER PUBLICATIONS

Notice of Allowance dated Jun. 2, 2014 for U.S. Appl. No. 13/276,687.
Office Action Non-Final dated Feb. 28, 2014 for U.S. Appl. No. 13/276,745.
International Search Report and Written Opinion dated Jul. 6, 2012 for PCT/US2011/059381.
Office Action Non-Final dated Aug. 6, 2013 for U.S. Appl. No. 13/151,471.
Restriction Requirement dated Jul. 5, 2013 for U.S. Appl. No. 13/151,488.
Office Action Non-Final dated Jun. 14, 2013 for U.S. Appl. No. 13/151,498.
Restriction Requirement dated Jun. 24, 2013 for U.S. Appl. No. 13/151,509.
Office Action Final dated Aug. 16, 2013 for U.S. Appl. No. 13/274,516.
Office Action Final dated Sep. 12, 2013 for U.S. Appl. No. 13/274,805.
Office Action Non-Final dated Jun. 14, 2013 for U.S. Appl. No. 13/274,830.
Office Action Final dated Aug. 29, 2013 for U.S. Appl. No. 13/275,563.
Office Action Non-Final dated Aug. 19, 2013 for U.S. Appl. No. 13/276,673.
Office Action Non-Final dated Jun. 12, 2013 for U.S. Appl. No. 13/276,687.
U.S. Appl. No. 13/151,509, filed Jun. 2, 2011, Smith et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
International Search Report and Written Opinion dated Jan. 26, 2012 for Application No. PCT/US2011/059212.
International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Machine Translation of the Abstract of German Application No. DE 102009013034.
Machine Translation of German Application No. DE 102008051866.
U.S. Appl. No. 12/576,776, filed Oct. 9, 2009, Boudreaux et al.
U.S. Appl. No. 13/151,471, filed Jun. 2, 2011, Stulen et al.
U.S. Appl. No. 13/151,481, filed Jun. 2, 2011, Yates et al.
U.S. Appl. No. 13/151,488, filed Jun. 2, 2011, Shelton, IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,512, filed Jun. 2, 2011, Houser et al.
U.S. Appl. No. 13/151,515, filed Jun. 2, 2011, Felder et al.
Notice of Allowance dated Dec. 6, 2013 for U.S. Appl. No. 13/151,471.
Office Action Final dated Nov. 21, 2013 for U.S. Appl. No. 13/151,498.
Office Action Non-Final dated Sep. 26, 2013 for U.S. Appl. No. 13/151,509.
Office Action Final dated Oct. 25, 2013 for U.S. Appl. No. 13/270,667.
Office Action Non-Final dated Nov. 21, 2013 for U.S. Appl. No. 13/271,352.
Office Action Non-Final dated Dec. 6, 2013 for U.S. Appl. No. 13/274,516.
Office Action Final dated Oct. 25, 2013 for U.S. Appl. No. 13/274,540.
Office Action Final dated Nov. 26, 2013 for U.S. Appl. No. 13/274,830.
Office Action Final dated Dec. 5, 2013 for U.S. Appl. No. 13/275,495.
Notice of Allowance dated Nov. 12, 2013 for U.S. Appl. No. 13/276,687.
Office Action Final dated Sep. 27, 2013 for U.S. Appl. No. 13/276,707.
Office Action Final dated Nov. 8, 2013 for U.S. Appl. No. 13/276,745.
International Search Report dated Jan. 26, 2012 for Application No. PCT/US11/059220.
International Search Report dated Feb. 1, 2012 for Application No. PCT/US11/059223.
International Search Report dated Jan. 12, 2012 for Application No. PCT/US11/059226.
International Search Report dated May 29, 2012 for Application No. PCT/US11/059358.
Restriction Requirement dated Dec. 11, 2012 for U.S. Appl. No. 13/151,481.
Office Action Non-Final dated Feb. 15, 2013 for U.S. Appl. No. 13/151,481.

(56) References Cited

OTHER PUBLICATIONS

Office Action Final dated Jun. 7, 2013 for U.S. Appl. No. 13/151,481.
Restriction Requirement dated Mar. 13, 2013 for U.S. Appl. No. 13/151,509.
Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Restriction Requirement dated Apr. 29, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
Office Action Non-Final dated Dec. 21, 2012 for U.S. Appl. No. 13/276,673.
Restriction Requirement dated Feb. 6, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
US Office Action, Notice of Allowance, dated Aug. 19, 2014 for U.S. Appl. No. 13/151,471.
US Office Action, Notice of Allowance, dated Nov. 21, 2014 for U.S. Appl. No. 13/151,471.
US Office Action, Non-Final, dated Aug. 14, 2014 for U.S. Appl. No. 13/151,481.
US Office Action, Non-Final, dated Nov. 7, 2014 for U.S. Appl. No. 13/151,488.
US Office Action, Notice of Allowance, dated Aug. 6, 2014 for U.S. Appl. No. 13/151,498.
US Office Action, Notice of Allowance, dated Nov. 21, 2014 for U.S. Appl. No. 13/151,498.
US Office Action, Non-Final, dated Nov. 6, 2014 for U.S. Appl. No. 13/151,503.
US Office Action, Non-Final, dated Jul. 9, 2014 for U.S. Appl. No. 13/151,509.
US Office Action, Notice of Allowance, dated Oct. 28, 2014 for U.S. Appl. No. 13/151,509.
US Office Action, Restriction Requirement, dated Jul. 11, 2014 for U.S. Appl. No. 13/269,870.
US Office Action, Non-Final, dated Jan. 5, 2015 for U.S. Appl. No. 13/269,870.
US Office Action, Non-Final, dated Jul. 29, 2014 for U.S. Appl. No. 13/270,667.
US Office Action, Notice of Allowance, dated Dec. 17, 2014 for U.S. Appl. No. 13/270,667.
US Office Action, Restriction Requirement, dated Jul. 9, 2014 for U.S. Appl. No. 13/270,684
US Office Action, Non-Final, dated Oct. 9, 2014 for U.S. Appl. No. 13/270,684
US Office Action, Restriction Requirement, dated Sep. 11, 2014 for U.S. Appl. No. 13/270,701.
US Office Action, Non-Final, dated Dec. 16, 2014 for U.S. Appl. No. 13/270,701.
US Office Action, Restriction Requirement, dated Sep. 25, 2014 for U.S. Appl. No. 13/271,352.
US Office Action, Restriction Requirement, dated Oct. 2, 2013 for U.S. Appl. No. 13/274,480.
US Office Action, Final, dated Jul. 17, 2014 for U.S. Appl. No. 13/274A80.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Notice of Allowance, dated Jan. 21, 2015 for U.S. Appl. No. 13/274,540.
US Office Action, Non-Final, dated Aug. 14, 2014 for U.S. Appl. No. 13/274,805.
US Office Action, Notice of Allowance, dated Nov. 28, 2014 for U.S. Appl. No. 13/274,805.
US Office Action, Notice of Allowance, dated Jan. 21, 2015 for U.S. Appl. No. 13/274,805.
US Office Action, Non-Final, dated Oct. 22, 2014 for U.S. Appl. No. 13/274,830.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Restriction Requirement, dated Jul. 9, 2014 for U.S. Appl. No. 13/276,660.
US Office Action, Non-Final, dated Aug. 14, 2014 for U.S. Appl. No. 13/276,673.
US Office Action, Notice of Allowance, dated Sep. 12, 2014 for U.S. Appl. No. 13/276,687.
US Office Action, Notice of Allowance, dated Dec. 23, 2014 for U.S. Appl. No. 13/276,687.
US Office Action, Non-Final, dated Aug. 20, 2014 for U.S. Appl. No. 13/276,725.
US Office Action, Notice of Allowance, dated Oct. 7, 2014 for U.S. Appl. No. 13/276,745.
US Office Action, Notice of Allowance, dated Dec. 19, 2014 for U.S. Appl. No. 13/276,745.
US Office Action, Restriction Requirement, dated Sep. 24, 2014 for U.S. Appl. No. 13/277,328.
US Office Action, Non-Final, dated Dec. 8, 2014 for U.S. Appl. No. 13/277,328.

\* cited by examiner

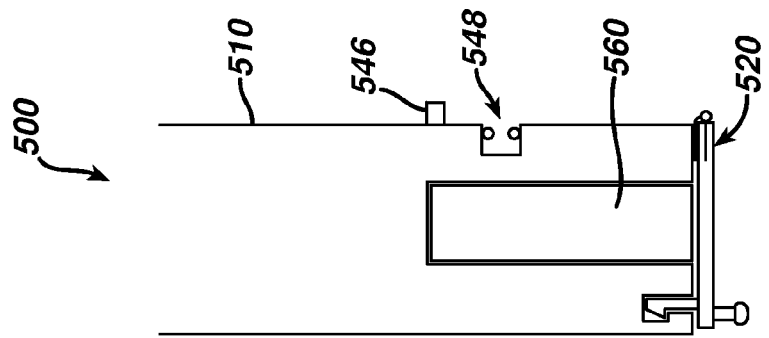
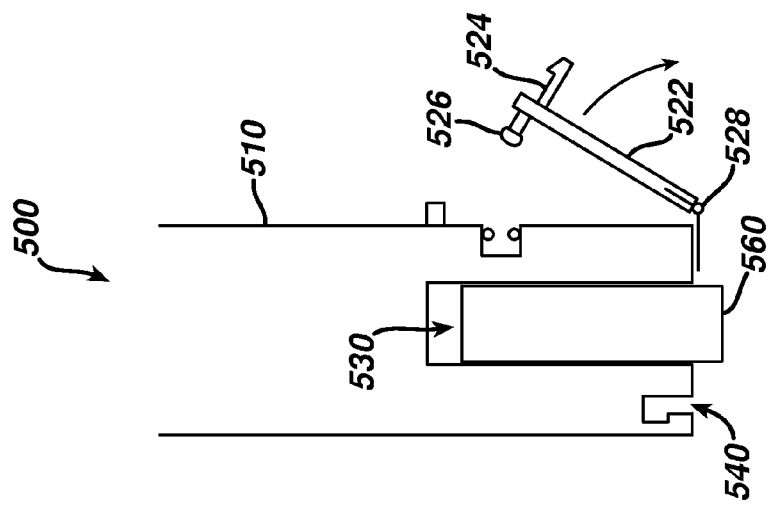
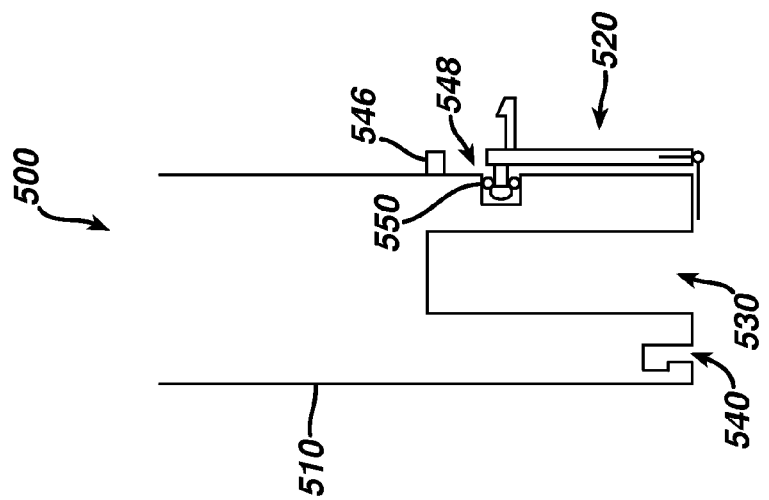

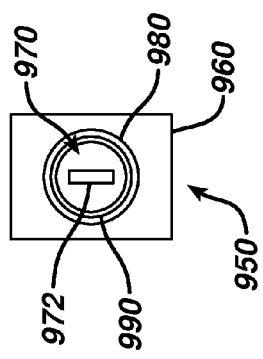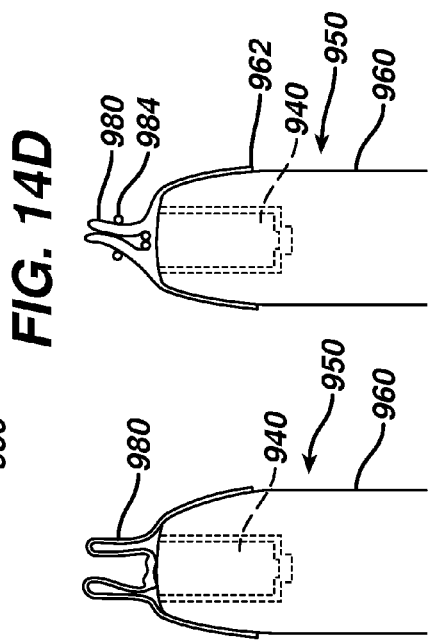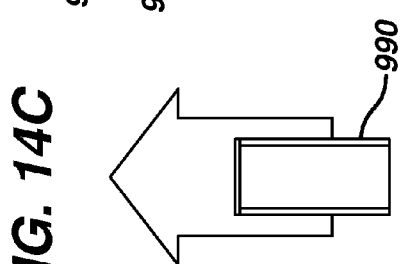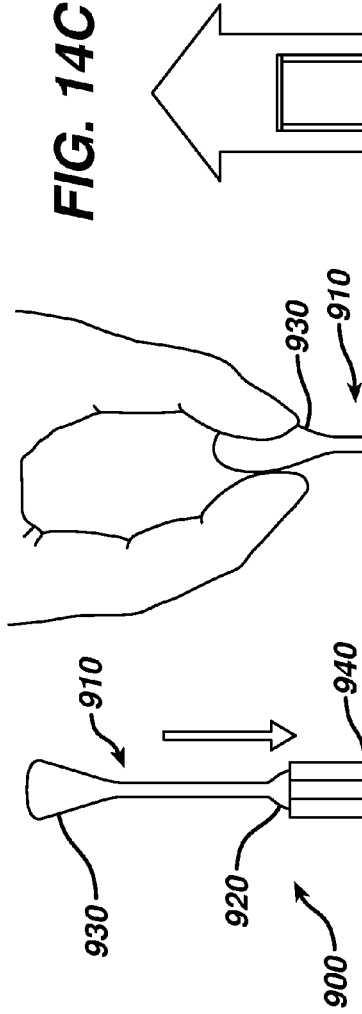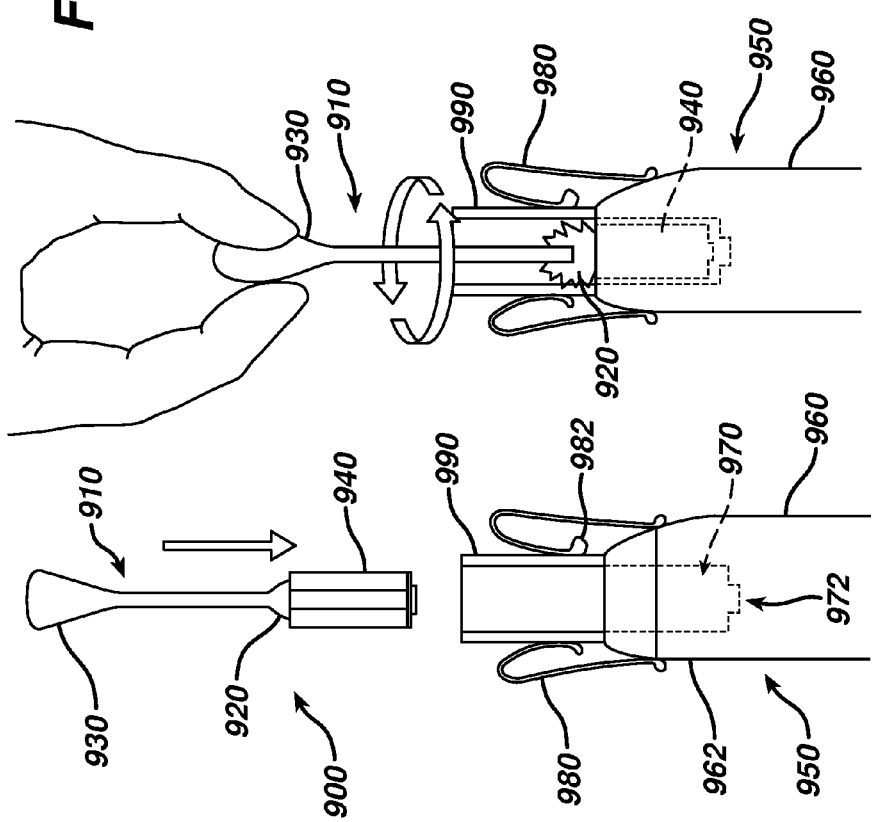

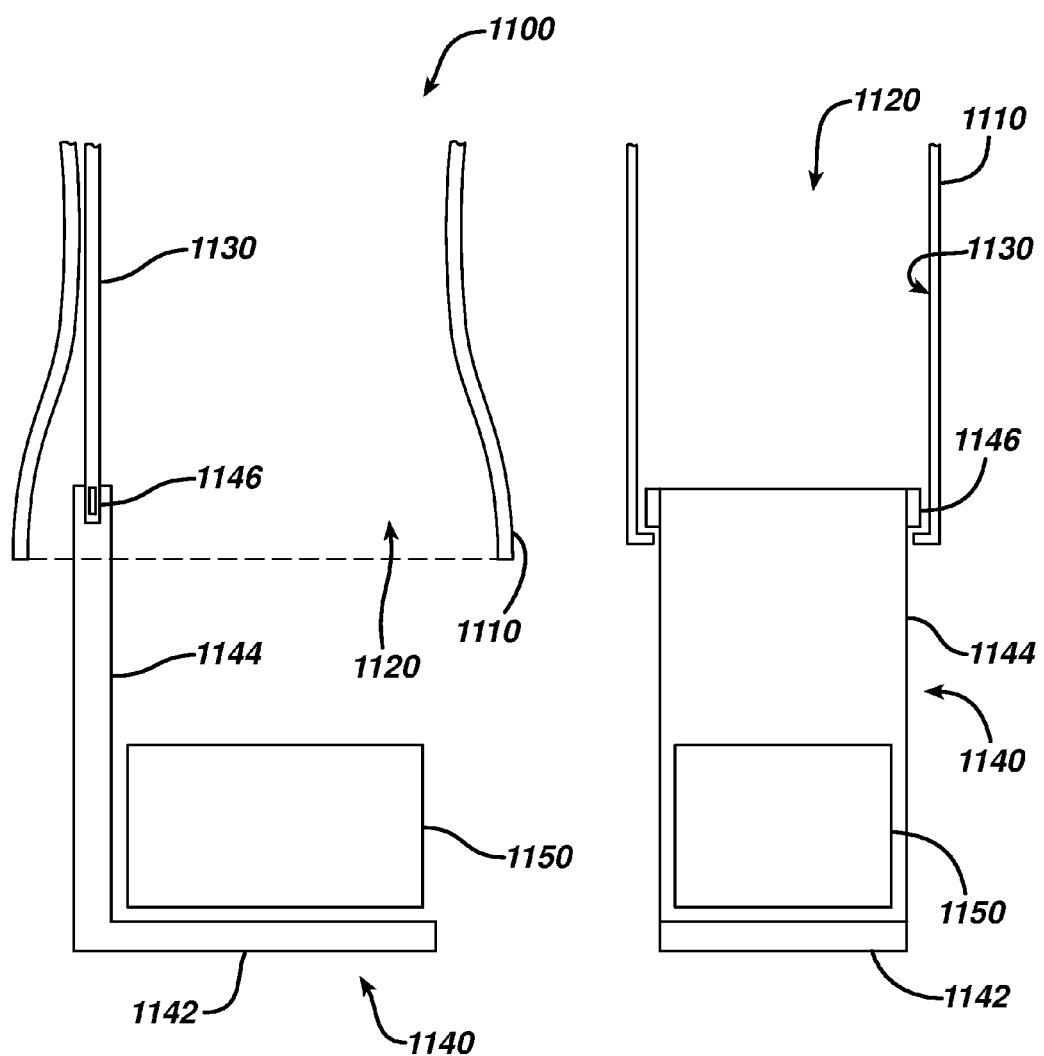

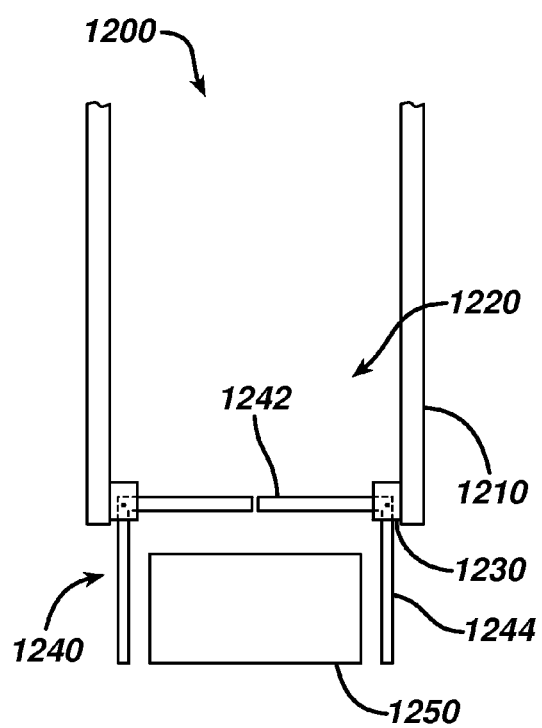
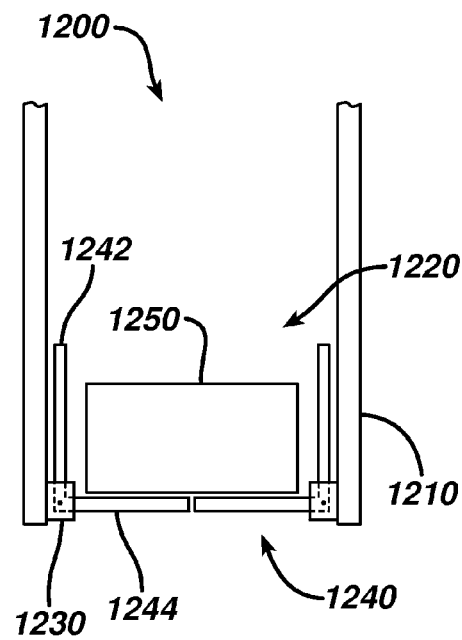
FIG. 20A  FIG. 20B

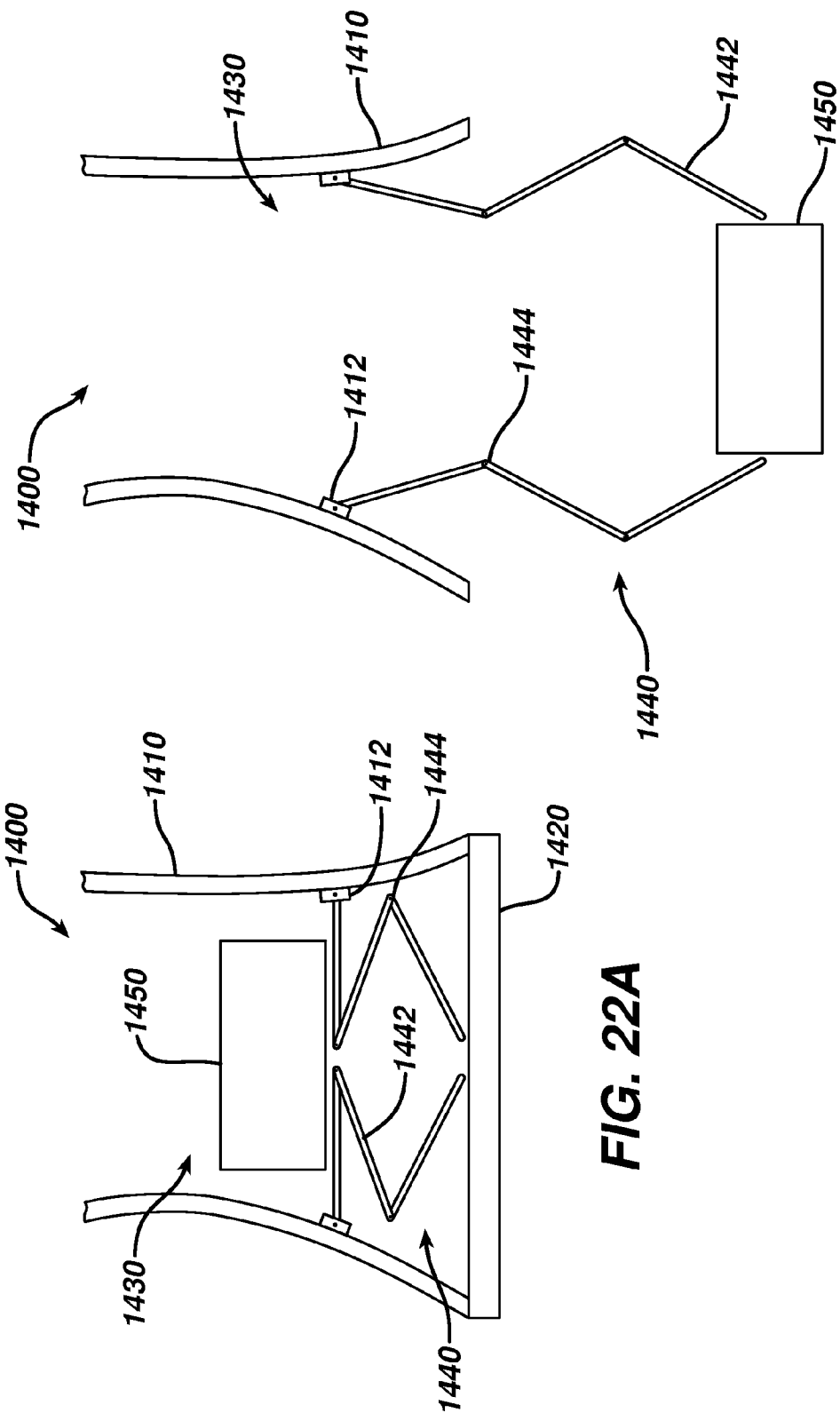

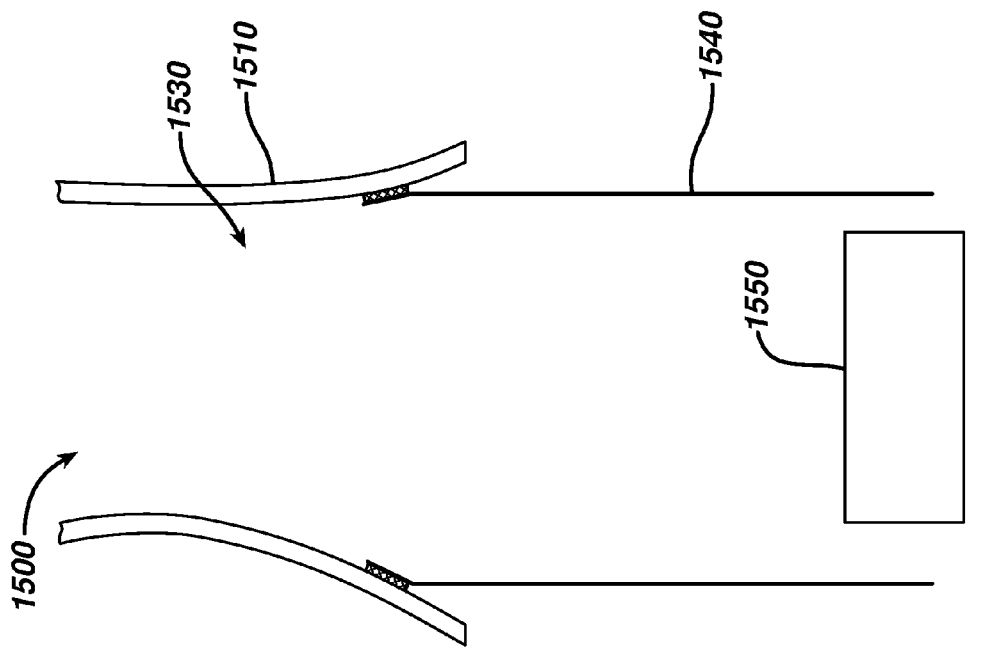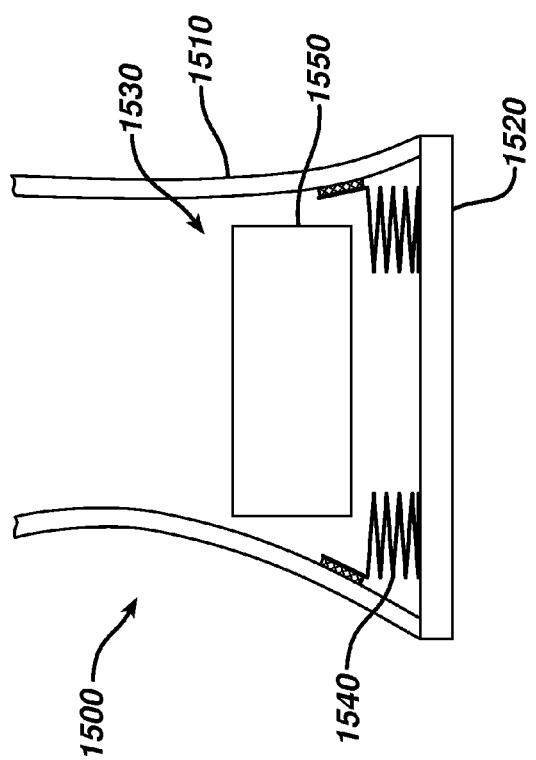

MEDICAL DEVICE WITH FEATURE FOR STERILE ACCEPTANCE OF NON-STERILE REUSABLE COMPONENT

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

Medical devices may be used during internal operations on a patient. During these operations, bodily fluids, such as blood, and/or tissue may come into contact with the medical device. Once blood and/or tissue come into contact with the medical device, the device may lose its sterility and may be contaminated. In general, medical devices may be constructed with little consideration for the potential of disassembly since the medical devices may be designed to be disposed of once contaminated after a single use. In some instances where portions may be made to be removable, they may generally consist of disposable parts for the device that detach to be thrown away before a new disposable part is used for a new patient. For some medical instruments lacking disposable parts, they may generally either be only used once or may need to be entirely resterilized before reuse.

With the advancement of the electronics industry, medical devices may be adapted to contain most, if not all, of the required components within the medical device. More specifically, some medical devices may be adapted to use an internal or attachable power source instead of requiring the device to be plugged into an external source by a cable. Merely exemplary devices that may be adapted to include a portable power source are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pub. No. 2009/0209990 entitled "Motorized Surgical Cutting and Fastening Instrument Having Handle Based Power Source," published Aug. 20, 2009, issued as U.S. Pat. No. 8,657,174 on Feb. 25, 2014, the disclosure of which is incorporated by reference herein; and U.S. Pub. No. 2010/0069940 entitled "Ultrasonic Device for Fingertip Control," published Mar. 18, 2010, the disclosure of which is incorporated by reference herein. Similarly, various ways in which medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

Electrically powered medical devices such as those referred to herein may require the use of high value or environmentally restricted disposable components to operate. The ability to reuse or reprocess these components over multiple uses may increase the value of the initial purchase by possibly spreading the cost of those components over the multiple uses. It may also be desirable in some settings to allow portable electronic components such as batteries to be recharged and/or be otherwise reprocessed between uses in sterile medical devices, without such electronic components having to be resterilized between uses in sterile medical devices, and without such devices contaminating sterile medical devices during re-use of the non-sterile electronic components. In addition or in the alternative, reclamation and reuse of the components may avoid or mitigate any environmental issues that may otherwise be associated with the disposal of the components after a single use. One potential approach may include reusing clean electrical components within multiple medical devices.

While several systems and methods have been made and used for component acceptance and release features for medical devices, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9A depicts a top cross-sectional view of another exemplary medical device feature, incorporating a releasable door assembly with the door assembly shown in an open position;

FIG. 9B depicts a top cross-sectional view of the feature of FIG. 9A, showing the door assembly as released;

FIG. 9C depicts a top cross-sectional view of the feature of FIG. 9A, showing the door assembly in a closed position;

FIG. 14A depicts a side cross-sectional view of another exemplary medical device feature, in an insertable component receiving configuration;

FIG. 14B depicts a side cross-sectional view of the feature of FIG. 14A, showing detachment of a handle from an insertable component as the component is inserted into the feature of FIG. 14A;

FIG. 14C depicts a side cross-sectional view of the feature of FIG. 14A, with a sterile tube being removed;

FIG. 14D depicts a side cross-sectional view of the feature of FIG. 14A, showing a closure member attached to a sterile flexible member;

FIG. 15 depicts a top view of the feature of FIG. 14A, in an insertable component receiving configuration;

FIG. 18 depicts a side cross-sectional view of another exemplary medical device feature, incorporating a lift assembly shown in an open position;

FIG. 19 depicts a front cross-sectional view of the feature of FIG. 18;

FIG. 20A depicts a side cross-sectional view of yet another exemplary medical device feature, incorporating a pair of L-shaped doors shown in an open position;

FIG. 20B depicts a side cross-sectional view of the feature of FIG. 20A, showing the pair of L-shaped doors in a closed position;

FIG. 22A depicts a side cross-sectional view of another feature for releasing an insertable component from within a medical device, with a pair of protective members shown in an initial position;

FIG. 22B depicts a side cross-sectional view of the feature of 22A, showing the protective members in a released position;

FIG. 23A depicts a side cross-sectional view of yet another exemplary feature for releasing an insertable component from within a medical device, with a pair of protective members shown in an initial position; and FIG. 23B depicts a side cross-sectional view of the feature of 23A, showing the pair of protective members in a released position.

Figure 1:
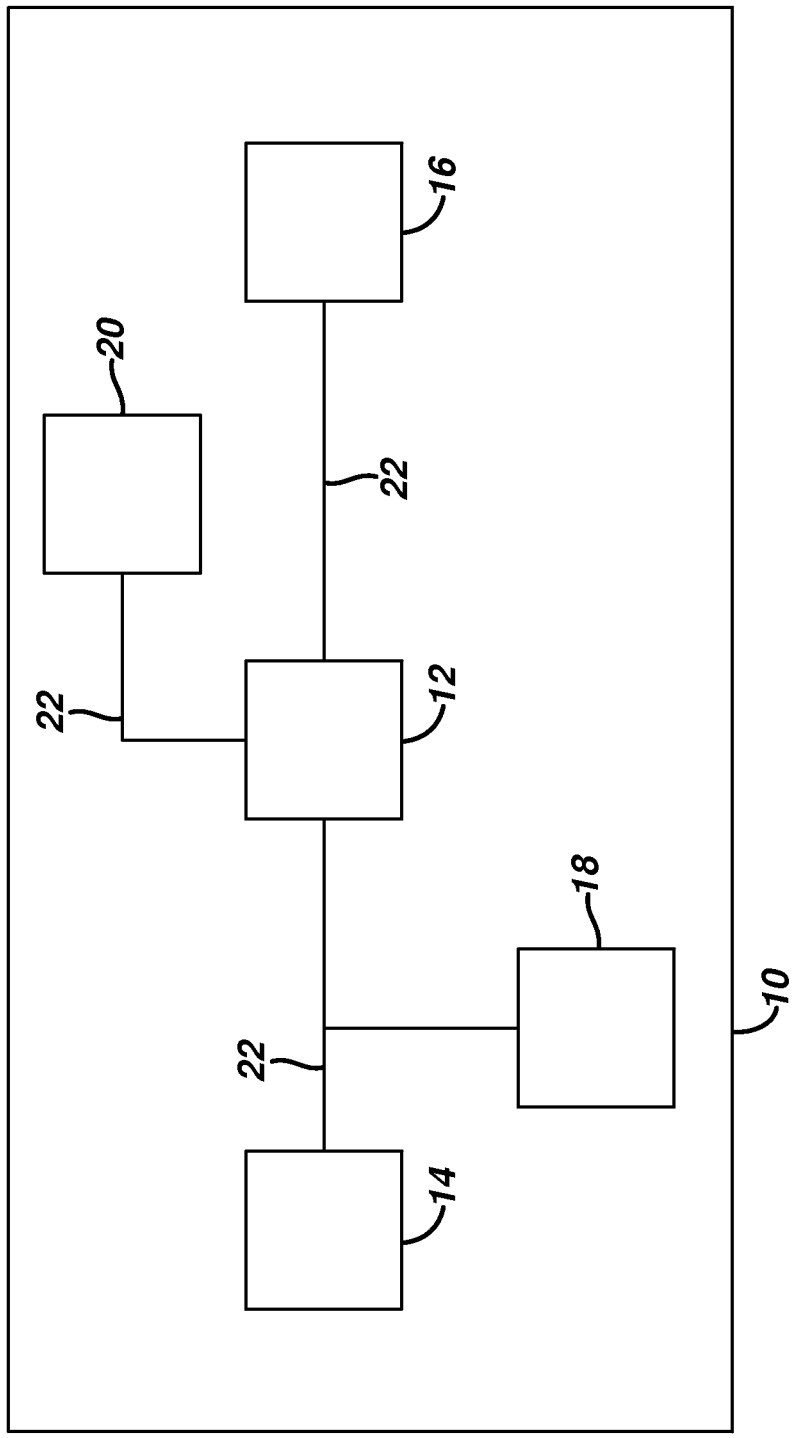
FIG. 1 depicts a schematic view of an exemplary medical device having an internal power source.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Medical Devices for Use with Insertable or Reclaimable Components

FIG. 1 shows components of an exemplary medical device (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired.

Figure 2:
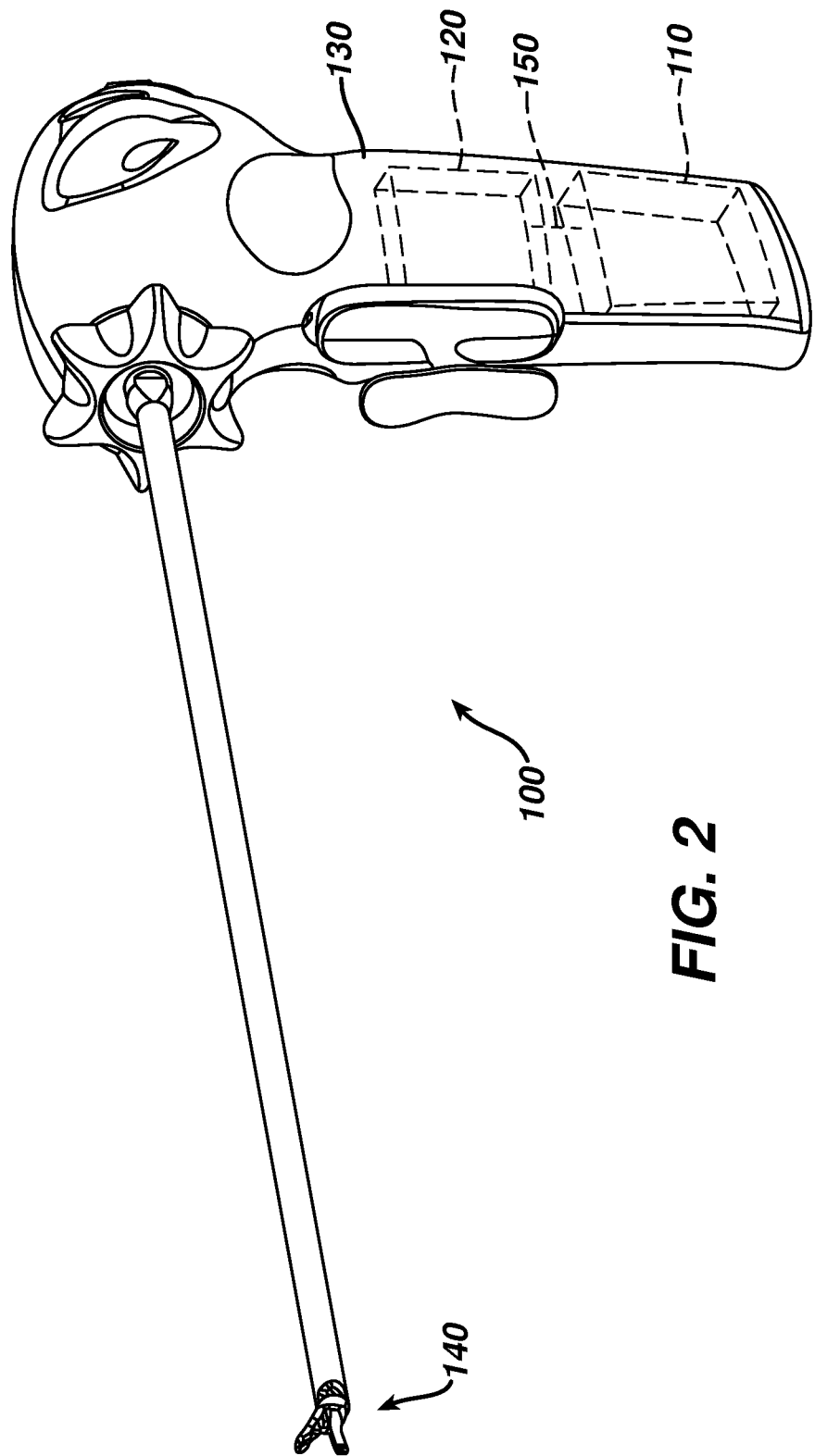
FIG. 2 depicts a perspective view of an exemplary medical device having an internal power source.

FIG. 2 depicts a merely exemplary form that medical device (10) may take. In particular, FIG. 2 shows a medical device (100) comprising a power source (110), a control module (120), a housing (130), end effector (140), and an electrical connection (150). In the present example, power source (110) is located internally within housing (130) of medical device (100). Alternatively, power source (110) may only partially extend into housing (130) and may be selectively attachable to a portion of housing (130). In yet a further exemplary configuration, a portion of housing (130) may extend into power source (110) and power source (110) may be selectively attachable to the portion of housing (130).

Power source (110) may also be configured to detach from medical device (100) and decouple from control module (120) or electrical connection (150). As a result, power source (110) may be completely separated from medical device (100) in some versions. As is readily apparent, this may allow the power source (110) to be removed to be recharged or reclaimed for resterilization and reuse, such as in accordance with various teachings herein. After recharging, or after an initial charge, power source (110) may be inserted or reinserted into medical device (100) and secured to housing (130) or internally within housing (130). Of course, medical device (100) may also allow power source (110) to be charged and/or recharged while power source (110) is still in or otherwise coupled relative to housing (130).

It should also be understood that control module (120) may be removed for servicing, testing, replacement, or any other purpose as will be apparent to one of ordinary skill in the art in view of the teachings herein. Further, end effector (140) may also be removable from medical device (100) for servicing, testing, replacement, or any other purpose as will be apparent to one of ordinary skill in the art in view of the teachings herein. While certain configurations of an exemplary medical device (100) have been described, various other ways in which medical device (100) may be configured will be apparent to those of ordinary skill in the art in view of the teachings herein. By way of example only, medical devices (10, 100) and/or any other medical device referred to herein may be constructed in accordance with at least some of the teachings of U.S. Pat. No. 6,500,176; U.S. Pat. No. 7,416,101; U.S. Pat. No. 7,738,971; U.S. Pub. No. 2006/0079874; U.S. Pub. No. 2007/0191713; U.S. Pub. No. 2007/0282333; U.S. Pub. No. 2008/0200940; U.S. Pub. No. 2009/0209990, issued as U.S. Pat. No. 8,657,174 on Feb. 25, 2014; U.S. Pub. No. 2010/0069940; and/or U.S. Provisional Application Ser. No. 61/410,603.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that various teachings herein may be readily combined with various teachings in any of the following patent applications, all of which are filed on even date herewith and the disclosures of all of which are incorporated by reference herein: U.S. patent application Ser. No. 13/151,471, entitled "Medical Device Packaging with Charging Interface," published as U.S. Pub. No. 2012/0112690 on May 10, 2012, issued as U.S. Pat. No. 9,000,720 on Apr. 7, 2015; U.S. patent application Ser. No. 13/151,481, entitled "Motor Driven Electrosurgical Device with Mechanical and Electrical Feedback," published as U.S. Pub. No. 2012/0116379 on May 10, 2012; U.S. patent application Ser. No. 13/151,488, entitled "Packaging for Reclaimable Component of a Medical Device," published as U.S. Pub. No. 2012/0111591 on May 10, 2012; U.S. patent application Ser. No. 13/151,498, entitled "Sterile Housing for Non-Sterile Medical Device Component," published as U.S. Pub. No. 2012/0115007 on May 10, 2012; U.S. patent application Ser. No. 13/151,503, entitled "Sterile Medical Instrument Charging Device," published as U.S. Pub. No. 2012/0116380 on May 10, 2012; U.S. patent application Ser. No. 13/151,509, entitled "Medical Device Packaging with Window for Insertion of Reusable Component," published as U.S. Pub. No. 2012/0110824 on May 10, 2012; and U.S. patent application Ser. No. 13/151,515, entitled "Sterile Package System for Medical Device," published as U.S. Pub. No. 2012/0305427 on Dec. 6, 2012. Various suitable ways in which teachings herein may be combined with teachings of the above-referenced patent applications, as well as various ways in which teachings of the above-referenced patent applications may be combined together with or without teachings herein, will be apparent to those of ordinary skill in the art.

II. Features for a Medical Device to Permit Sterile Insertion and/or Removal of a Non-Sterile Internal Component For medical devices utilizing recoverable components, the ability to reuse those components over multiple uses may increase the value of the initial purchase by possibly spreading the cost of those components over the multiple uses. In addition or in the alternative, if environmental restrictions limit the disposal of certain components, the ability to remove those components from the device may permit the shipping of those components back to a manufacturer for recycling or proper disposal. One approach may include reusing non-sterile components within multiple devices by inserting the components into a medical device having a feature that permits the insertion of those components while maintaining the sterility of the medical device. Accordingly, the following examples relate to various illustrative ways in which to secure non-sterile components in medical devices with various features.

A. Medical Device with Threaded Covers

Figure 3:
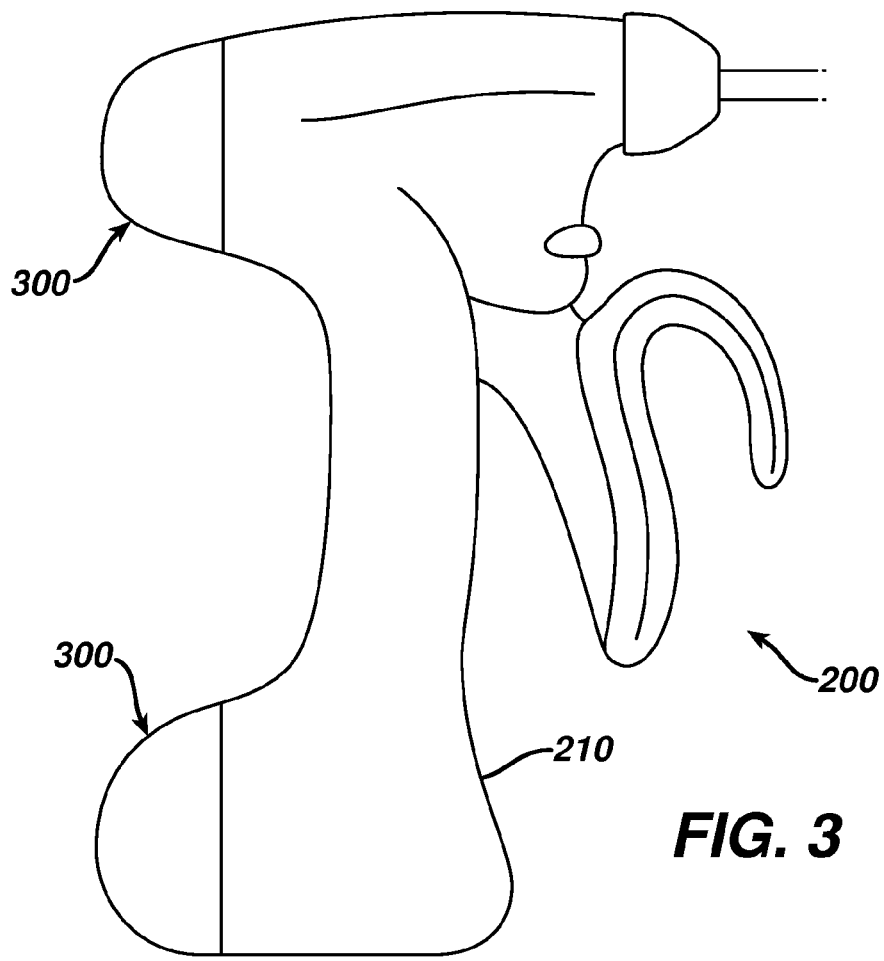
FIG. 3 depicts a side view of an exemplary medical device having a feature for securing insertable components within insertion recesses of the medical device.
Figure 4:
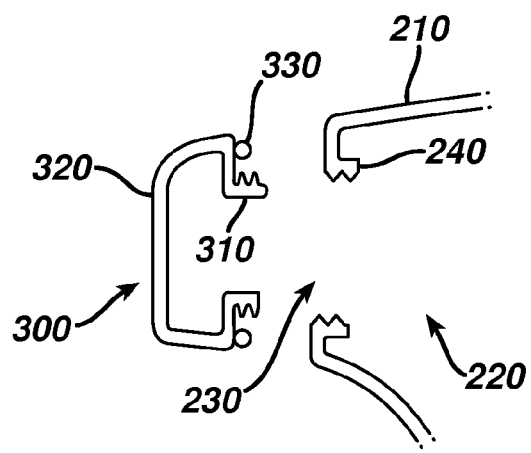
FIG. 4 depicts a partial side cross-sectional view of the feature of FIG. 3.
Figure 5:
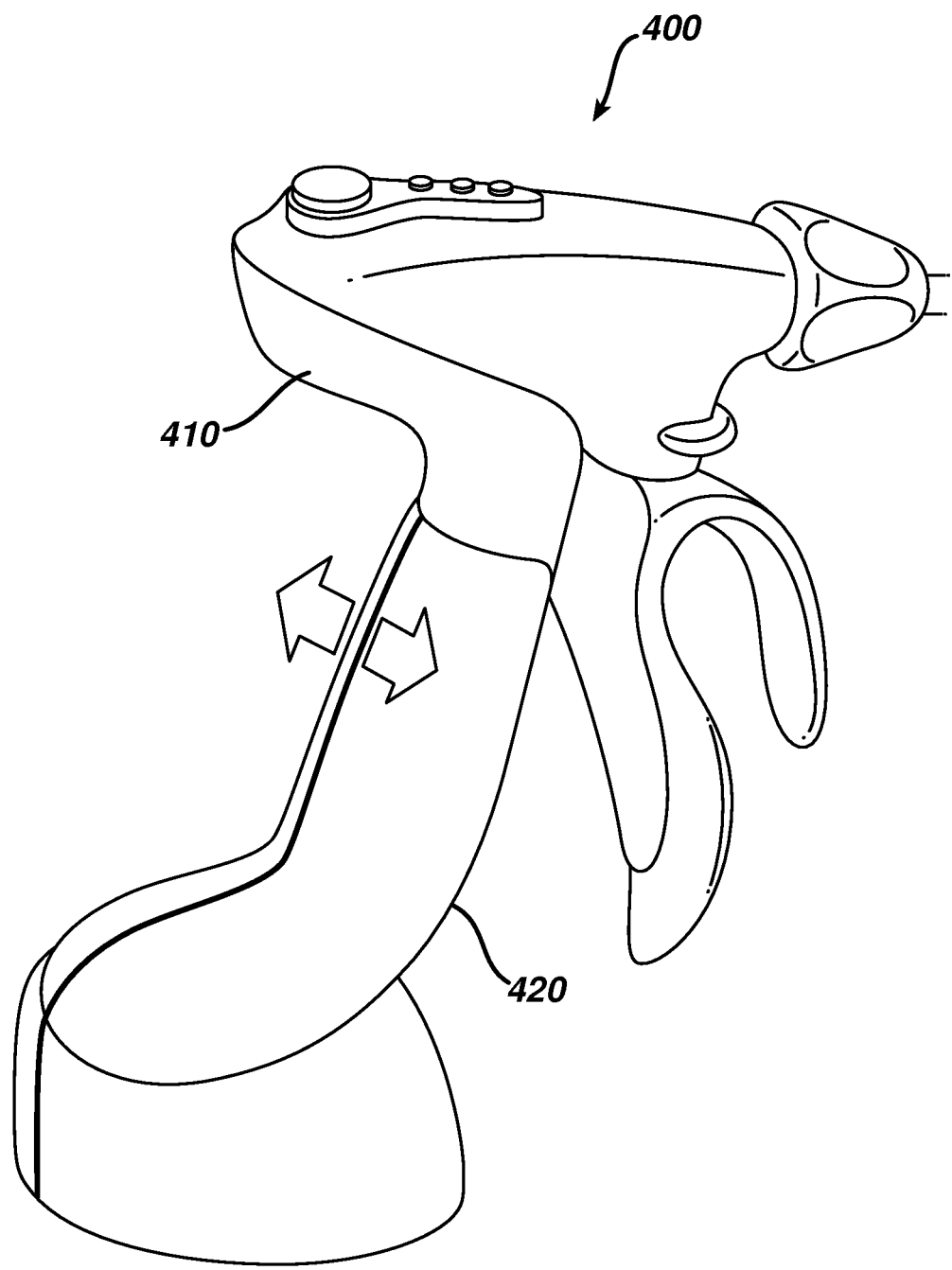
FIG. 5 depicts a perspective view of another exemplary feature for securing an insertable component within an insertion recess of a medical device.
Figure 6:
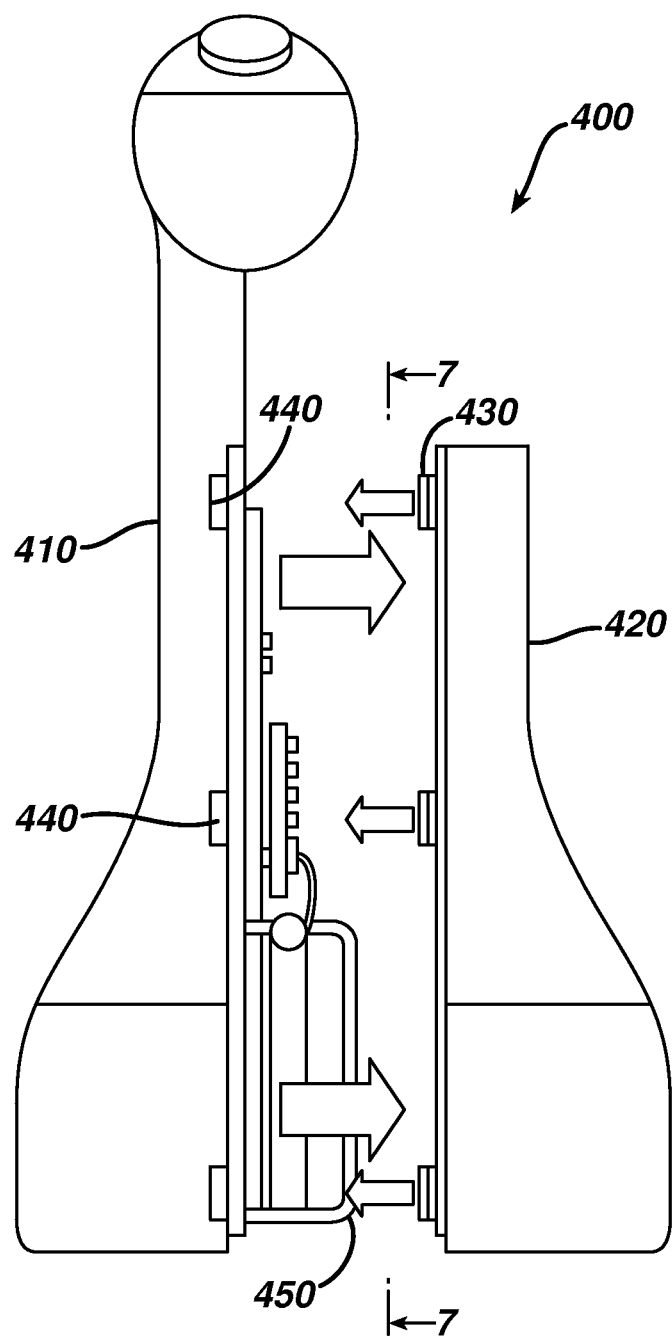
FIG. 6 depicts an exploded rear view of the medical device of FIG. 5, with the feature detached.
Figure 7:
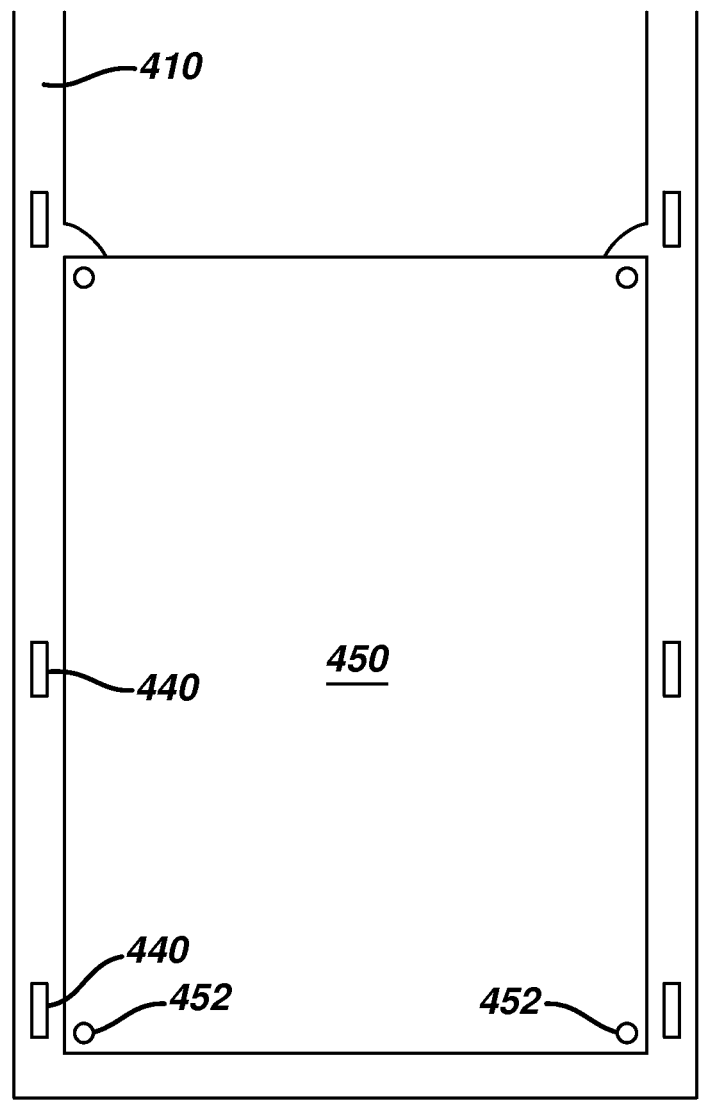
FIG. 7 depicts a sectional view of the medical device of FIG. 5, with the feature omitted.

FIGS. 3-4 show an exemplary medical device (200) that may be constructed in accordance with at least some of the teachings of medical devices (10, 100), as previously discussed herein, or medical device (200) may have any other suitable configuration as will be apparent to one of ordinary skill in the art in view of the teachings herein. In the present example, medical device (200) comprises a housing (210). Housing (210) at least partially defines a component recess (220) that is configured to receive an insertable component (not shown). By way of example only, the insertable component may comprise a power source, such as one of the types of batteries previously discussed herein, a plurality of batteries in the form of a battery pack, a control module, a printed circuit board, an ultrasonic transducer, and/or any other insertable component or combination of components as will be apparent to those of ordinary skill in the art in view of the teachings herein. Component recess (220) of exemplary medical device (200) is a substantially open cavity within medical device (200). However, it should be understood that component recess (220) may be sized to accommodate only an insertable component, a plurality of various insertable components, and/or have any other suitable configuration as will be apparent to one of ordinary skill in the art in light of the teachings herein. It should also be understood that the sterile medical device (200) may receive the insertable component without the insertable component necessarily sterile; and that the sterility of the exterior of medical device (200) will not be compromised by receipt of a non-sterile insertable component in component recess (220). Housing (210) may be made from a variety of materials including plastics, polyethylene terephthalate glycol (or PETG), thermoplastic polymer resins, or any other suitable rigid material for housing (210) of medical device (200). Various other materials and configurations for housing (210) may be provided as will be apparent to those of ordinary skill in the art in view of the teachings herein.

Housing (210) of medical device (200) of the present example further comprises a housing opening (230) sized to permit the passage of an insertable component through housing opening (230) and into component recess (220) of medical device (200). In the present example, housing opening (230) is circular in shape, though it should be understood that housing opening (230) may take a variety of geometrical configurations including rectangular, square, triangular, hexagonal, or any other configuration suitable for insertion of an insertable component into medical device (200) as will be apparent to one of ordinary skill in the art in light of the teachings herein. In the present example, two housing openings (230) are located on a rear portion of medical device (200), though it should be understood that housing openings (230) may be located at a variety of locations on housing (210) including the side, front, bottom, or top surfaces of housing (210) or any other suitable location as will be apparent to those of ordinary skill in the art in light of the teachings herein. Housing (210) of the present example further comprises device threading (240) encircling the perimeter of housing opening (230). Device threading (240) is configured to complement threading (310) of cap (300), as will be described below. It should be understood that device threading (240) is merely optional and other attachment configurations may be used to attach cap (300) to medical device (200). Merely exemplary alternative configurations include resilient snap-on members, bolt and nut combinations, friction fit attachments, or other suitable attachment configurations as will be readily apparent to one of ordinary skill in the art in view of the teachings herein. Various other configurations for housing opening (230) and/or device threading (240) will also be apparent to those of ordinary skill in the art in view of the teachings herein.

Each cap (300) is configured to seal its respective housing opening (230) of medical device (200) once the insertable components have been inserted into component recesses (220). Cap (300) may be made from a variety of materials including plastics, PETG, thermoplastic polymer resins, or any other suitable rigid material for use with cap (300) as will be apparent to one of ordinary skill in the art in light of the teachings herein. Cap (300) of the present example comprises a cap body (320) and cap threading (310). Cap body (320) is sized and configured such that when cap (300) is inserted into housing opening (230), cap (300) substantially seals component recess (220) of medical device (200). In the present example, cap body (320) is cylindrical in shape and is configured to correspond to housing opening (230), though it should be understood that cap body (320) may be any other geometric shape corresponding to housing opening (230) as will be apparent to those of ordinary skill in the art in light of the teachings herein. Cap threading (310) is configured to complement device threading (240) of medical device (200). It should be understood that cap (300) may alternatively be coupled to medical device (200) through a variety of other suitable configurations, including mechanical attachments such as snap-on or friction fit attachment, adhesive attachment; by adhesive attachments; or by any other suitable attachment method as will be apparent to those of ordinary skill in the art in view of the teachings herein.

Cap (300) may further comprise a cap seal (330) that is sized and configured to substantially conform to the shape of cap (300) at the interface between cap (300) and housing (210). In the present example, cap seal (330) is an o-ring type seal. Cap seal (330) is configured such that when cap (300) is coupled to medical device (200), cap seal (330) hermetically seals cap (300) with housing (210), thereby preventing fluid transfer into or out of component recess (220) of medical device (200). Cap seal (300) may be made from a variety of materials, including natural rubber, silicone, neoprene, polytetrafluoroethylene (or PTFE), or other suitable sealing materials and may be configured according to other suitable configurations as will be apparent to those of ordinary skill in the art in view of the teachings herein.

When a user desires to insert a non-sterile insertable component for use with medical device (200), initially caps (300) are detached from medical device (200) thereby exposing housing openings (230) and component recesses (220) therein. In the present example, caps (300) are unscrewed from device threading (240) of medical device (200). It should be understood that medical device (200) may be provided without caps (300) initially attached. With component recesses (220) exposed, a user may hold the medical device (200) while the non-sterile insertable components are inserted or dropped into component recesses (220), thereby limiting the potential for contamination of the exterior of medical device (200). Once the non-sterile insertable components are within component recesses (220) (e.g., a battery in the lower component recess (220) and an ultrasonic transducer in the upper component recess (220), etc.), the user reattaches caps (300) to seal the non-sterile insertable components within medical device (200). If cap seal (330) is provided, the user may tighten caps (300) to a desired torque to ensure that each seal (330) forms a hermetic seal. With the non-sterile insertable components secured within medical device (200) by caps (300), a user may use medical device (200) for a medical procedure, without the sterility of medical device (200) being compromised by the non-sterile insertable components. Of course, the insertable components may in fact be sterile before they are inserted in medical device (200).

To retrieve the non-sterile insertable components from used medical device (200), initially the user detaches caps (300) from used medical device (200), thereby exposing component recesses (220) that are accessible through housing openings (230). In the present example, caps (300) are unscrewed from device threading (240). To remove the non-sterile insertable components the user may either rotate used medical device (200) until the non-sterile insertable components drop out of component recesses (220) by the force of gravity, or the user's clean hand may retrieve the non-sterile insertable components from within component recesses (220). As a result, the non-sterile insertable components may be inserted and removed from medical device (200) while remaining clean (or at least free from contact with bodily fluids), which may permit a user to reuse those components multiple times and/or to retrieve the components for reclamation. Once the non-sterile insertable components are removed, medical device (200) may be disposed of or sent for reclamation. While some configurations for medical device (200) and cap (300) have been described, various other configurations may be provided as will be apparent to those of ordinary skill in the art in view of the teachings herein.

B. Medical Device with Snap-Fit Cover

FIGS. 5-8 show an exemplary alternative medical device (400) that may be constructed in accordance with at least some of the teachings of medical devices (10, 100), as previously discussed herein, though it should be understood that medical device (400) may have any other suitable configuration as will be apparent to one of ordinary skill in the art in view of the teachings herein. In the present example, medical device (400) comprises a primary housing (410) and a cover (420). Primary housing (410) defines a component recess that is configured to receive an insertable component (450). By way of example only, insertable component (450) may comprise a power source, such as one of the types of batteries previously discussed herein, a plurality of batteries in the form of a battery pack, a control module, a printed circuit board, an ultrasonic transducer, and/or any other insertable component or combination of components as will be apparent to those of ordinary skill in the art in view of the teachings herein. In the present example, insertable component (450) is shown as a battery pack and circuit board that is coupled to primary housing (410) by a plurality of mounting members (452). Insertable component (450) may be coupled to primary housing (410) by a variety of mounting members (452) including screws, bolts, snap-fit connections, or any other suitable form of mounting member (452) as will be apparent to one of ordinary skill in the art in view of the teachings herein. Alternatively, insertable component (450) may not be coupled to primary housing (410) by mounting members (452); and may instead be substantially free within the component recess and be secured only after coupling cover (420) to primary housing (410). Cover (420) is configured to removably couple to primary housing (410) and cover (420) is sized and configured to cooperatively encase insertable component (450) when coupled to primary housing (410).

Figure 8:
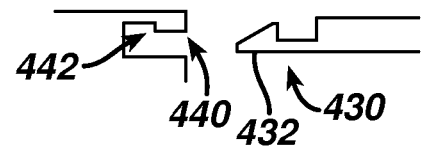
FIG. 8 depicts a partial cross-sectional view of a cantilever snap and recess of the feature of the medical device of FIG. 5.

To couple cover (420) to primary housing (410), cover (420) comprises a plurality of resilient cantilever members (430) and primary housing (410) comprises a plurality of recesses (440) configured to couple to resilient cantilever members (430). As shown in FIG. 8, an exemplary recess (440) comprises a retention portion (442) and resilient cantilever member (430) comprises a barbed insertable head (432). Retention portion (442) and insertable head (432) are configured to couple and retain cover (420) against primary housing (410) when insertable head (432) is inserted into retention portion (442). Optionally, a seal (not shown) may be provided with cover (420) to further ensure that insertable component (450) contained within medical device (400) is not contaminated by body fluids or other fluids during use of medical device (400). Both primary housing (410) and cover (420) may be made from a variety of materials including plastics, polyethylene terephthalate glycol (or PETG), thermoplastic polymer resins, or any other suitable rigid or semi-rigid material for the primary housing (410) and cover (420). Various other configurations for primary housing (410) and cover (420) may be provided as will be apparent to those of ordinary skill in the art in view of the teachings herein.

When a user desires to insert an insertable component (450) for use with medical device (400), initially cover (420) is detached from primary housing (410) thereby exposing the component recess therein. In the present example, resilient cantilever members (430) of cover (420) are bent to permit insertable head (432) to decouple from retention portions (442) of recesses (440). It should be understood that medical device (400) may also be provided without cover (420) initially attached. In the present example, a user then couples insertable component (450) by mounting members (452) (such as screws) to primary housing (410). If mounting members (452) are not used, the user may simply place the insertable component (450) into the component recess of primary housing (410) prior to coupling cover (420). Once the insertable component (450) is within the component recess, the user reattaches cover (420) to seal the insertable component within medical device (400). In the present example, insertable heads (432) deform and then snap into retention portions (442) with resilient cantilever members (430) are inserted into recesses (440). With the insertable component (450) secured within medical device (400) by cover (420), a user then uses medical device (400) for a medical procedure. In the present example, cover (420) and primary housing (410) protect insertable component (450) from potential contamination while medical device (400) is in use.

To retrieve insertable component (450) from used medical device (400), initially the user detaches cover (420) from primary housing (410), thereby exposing insertable component (450) therein. In the present example, resilient cantilever members (430) are bent such that insertable heads (432) decouple from retention portions (442) of recesses (440). Alternatively, the user may break resilient cantilever members (430) while insertable heads (432) are still coupled within retention portions (442). Mounting members (452) of the present example are then detached from insertable component (450), thereby permitting insertable component (450) to be removed. The user may then tip insertable component (450) out of primary housing (410) or the user may remove insertable component (450) with a clean hand. As a result, insertable component (450) may be inserted and removed from medical device (400) while remaining clean (or at least substantially free of body fluids, etc.). This permits a user to reuse insertable component (450) multiple times and/or to retrieve insertable component (450) for reclamation. This also permits a non-sterile insertable component (450) to be used in medical device (400) without compromising the sterility of the exterior of medical device (400). While some configurations for medical device (400), primary housing (410), and cover (420) have been described, various other configurations may be provided as will be apparent to those of ordinary skill in the art in view of the teachings herein.

C. Medical Device with Hinged Door Closures

FIGS. 9A-9C depict yet another exemplary alternative feature for a medical device (500) that may be constructed in accordance with at least some of the teachings of medical devices (10, 100), as previously discussed herein, or medical device (500) may have any other suitable configuration as will be apparent to one of ordinary skill in the art in view of the teachings herein. Medical device (500) of the present example comprises a primary housing (510) and a door assembly (520). Primary housing (510) defines an insertion recess (530) and a snap recess (540), and further includes a release button (546) and a door release recess (548), though it should be understood that snap recess (540), release button (546), and door release recess (548) are merely optional. Primary housing (510) may be made from a variety of materials including plastics, polyethylene terephthalate glycol (or PETG), thermoplastic polymer resins, or any other suitable rigid or semi-rigid material for the primary housing (510). Insertion recess (530) is sized and configured to receive an insertable component (560). By way of example only, insertable component (560) may comprise a power source, such as one of the types of batteries previously discussed herein, a plurality of batteries in the form of a battery pack, a control module, a printed circuit board, an ultrasonic transducer, and/or any other insertable component (560) or combination of components as will be apparent to those of ordinary skill in the art in view of the teachings herein. Insertion recess (530) may further comprise additional components, such as electrical connections or mechanical attachments to couple insertable component (560) within medical device (500).

In the present example, insertion recess (530) is formed on a rear surface of primary housing (510), but it should be understood that insertion recess (530) may be located at any suitable location on primary housing (510) such as a top, side, front, rear, or bottom surface of primary housing (510). Additionally, primary housing (510) may further comprise a seal (not shown) encircling the perimeter of insertion recess (530) such that when door assembly (520) is in a closed position, the seal forms a hermetic seal between primary housing (510) and door (522). Alternatively, the seal may be attached to door (522) instead of primary housing (510). While some configurations for primary housing (510) have been described, various other configurations may be provided as will be apparent to those of ordinary skill in the art in view of the teachings herein.

Referring to FIG. 9B, door assembly (520) is hingedly attached to primary housing (510) and is configured to enclose insertable component (560) within component recess (530) when door assembly (520) is in a closed position. Door assembly (520) comprises a door (522), a resilient cantilever member (524), a release member (526), and a resilient hinge (528), though it should be understood that resilient cantilever member (524) and release member (526) are merely optional. Door (522) is sized and configured to substantially seal insertion recess (530) within primary housing (510) when door (522) in the closed position, as seen in FIG. 9C. Resilient hinge (528) hingedly attaches door (522) to primary housing (510) and urges door assembly (520) from an open position to a closed position once released from door release recess (548), as will be described below. In the present example, resilient hinge (528) is a spring-loaded hinge though other suitable resilient hinges (528) will be apparent to one of ordinary skill in the art in view of the teachings herein. Resilient cantilever member (524) of the present example extends from a distal surface of door (522) and is configured to couple with snap recess (540) to retain door (522) in the closed position while medical device (500) is in use. An optional release slider (not shown) may be included on door (522) to decouple resilient cantilever member (524) from snap recess (540). Alternatively, the release slider may be mounted to primary housing (510) to actuate resilient cantilever member (524) within snap recess (540) to decouple resilient cantilever (524). Resilient cantilever member (524) and snap recess (540) may be constructed in accordance with at least some of the teachings of resilient cantilever member (430) and recess (440), as previously discussed herein; or resilient cantilever member (524) and snap recess (540) may have any other suitable configuration as will be apparent to one of ordinary skill in the art in view of the teachings herein. Release member (526) extends from a proximal surface of door (522) and is configured to releasably couple with door release recess (548) to retain door assembly (520) in the open position, as seen in FIG. 9A.

Referring back to FIG. 9A, door release recess (548) is configured to releasably couple to release member (526) to keep door assembly (520) in the open position prior to and after use of medical device (500). One merely exemplary door release recess (548) comprises a resilient detent feature (550) configured to couple with release member (526) when release member (526) is inserted into door release recess (548), such as a spring-loaded ball bearing assembly. In the present example, release button (546) is located on the side surface of primary housing (510), near door release recess (548), though it should be understood that this is merely optional and release button (546) may be mounted on any surface of primary housing (510). Release button (546) is coupled to door release recess (548) and is configured to actuate resilient detent feature (550) from a secured position to a released position such that when release button (546) is pressed resilient detent feature (550) is moved to the released position, thereby decoupling release member (526) from within door release recess (548). One merely exemplary method to couple release button (546) to resilient detent feature (550) is to mechanically link release button to resilient detent feature (550). In the instance that resilient detent feature (550) comprises a spring-loaded ball bearing assembly, the mechanical linkage may be one that compresses the spring away from door release recess (548) such that the ball bearing may recede into an opening (not shown), allowing release member (526) to exit door release recess (548). Alternatively, release button (546) may be coupled to an electrical component that operates a servo motor to actuate resilient detent feature (550). In this instance, release button (546) may be mounted at any location on medical device (500) or release button (546) may be a remotely operable unit. Further still, release button (546) may be entirely omitted and internal software may run a routine to operate a servo motor to actuate resilient detent feature (550). While various configurations for door release recess (548) and release button (546) have been described, yet other suitable configurations will be apparent to those of ordinary skill in the art in view of the teachings herein.

Initially, medical device (500) without insertable component (560) inserted therein is sterilized. In one exemplary sterilization technique, medical device (500) is placed in a field of radiation that can penetrate medical device (500), such as gamma radiation, x-rays, or high-energy electrons. The radiation may kill bacteria on medical device (500) and within insertion recess (530). Alternatively, medical device (500) may be sterilized using any other technique known in the art, including but not limited to beta or gamma radiation, ethylene oxide, electron beam sterilization, or steam. Various other suitable sterilization methods that may be provided will be apparent to those of ordinary skill in the art in view of the teachings herein. It should also be understood that any other medical device referred to herein may be sterilized using any of the techniques referred to above and/or using any other suitable techniques.

When a user desires to use medical device (500), initially the door assembly (520) is either preset in the open position of FIG. 9A or a sterile user, such as a nurse, actuates door assembly (520) to the open position and inserts release member (526) into door release recess (548) to retain door assembly (520) in the open position. Insertable component (560) is then inserted into insertion recess (530). If insertable component (560) is non-sterile, then insertable component (560) may simply be dropped into insertion recess (530) to potentially avoid contamination of the sterile exterior of medical device (500). In the present example, release button (546) is then depressed to actuate resilient detent feature (550) to a released position, thereby decoupling release member (526) from resilient detent feature (550). When release member (526) is decoupled from door release recess (548), resilient hinge (528) actuates door assembly (520) from the open position to the closed position, as seen in FIGS. 9A-9C. Resilient hinge (528) may be configured to apply a sufficient force to insert resilient cantilever member (524) into snap recess (540); or at least position cantilever member (524) adjacent to snap recess (540) such that the user must push cantilever member (524) fully into snap recess (540). Resilient cantilever member (524) couples with snap recess (540) to secure door assembly (520) to primary housing (510), thereby sealing insertable component (560) within insertion recess (530). Thus, after a non-sterile insertable component (560) is initially inserted, the user may avoid contaminating the exterior of medical device (500) by the automated closing of door assembly (520). A user may then use medical device (500) for a medical procedure while door assembly (520) keeps insertable component (560) substantially clean (e.g., free of body fluids and/or other fluids) within medical device (500).

To retrieve insertable component (560) from within used medical device (500), initially resilient cantilever member (526) is decoupled from snap recess (540). This may be accomplished by simply applying a sufficient force to overcome the resistance within the recess or by actuating a slide release, if provided. Alternatively, resilient cantilever member (526) may be configured to break apart when a sufficient force is applied, thereby leaving a portion of resilient cantilever member (526) within snap recess (540) while door assembly (520) is actuated into the open position. As yet another merely illustrative alternative, a separate button or other actuator (e.g., release button (546), etc.) may be used to release cantilever member (526) from snap recess (540). Door assembly (520) is then secured in the open position by reinserting release member (526) into door release recess (548). When inserted therein, resilient detent feature (550) actuates and then retains release member (526) within door release recess (548). With door assembly (522) secured in the open position, the user may simply tip medical device (500) to permit gravity to slide insertable component (550) out of medical device (500). Alternatively, a separate person, such as a nurse, may remove the non-sterile, but clean (e.g., substantially free of body fluids, etc.), insertable component (560) from insertion recess (530). Insertable component (550) may then be reclaimed and/or recharged for reuse; or otherwise be disposed of separately from medical device (500). Thus, a non-sterile insertable component may be used with a medical device while maintaining the sterility of the exterior of the medical device and also not contaminating the insertable component when removed from a used device.

Alternative door assemblies may also be implemented with medical device (500). One specific exemplary alternative door assembly includes two doors hingedly attached to the sides of primary housing (510). The door assembly may be configured to be butterfly doors. Accordingly when the two doors close, the doors cooperatively couple to enclose insertion recess (530) of medical device (500). This alternative door assembly may include additional components, such as resilient hinges (528), release members (526), door release recesses (548), release buttons (546), and/or any other suitable components as previously described herein.

Yet another exemplary alternative door assembly includes a garage door type door assembly. In this configuration, the door comprises a flat planar member that is slidably mounted within medical device (500). Primary housing (510) comprises an interior door recess that is coplanar with and offset from a rear surface of primary housing (510). The interior door recess further comprises a pair of tracks into which a portion of the door may fit into and slidably travel along. Primary housing (510) may further include a resilient member within the door recess, such as a spring, that is configured to apply a force to actuate the door from an open position to a closed position. Accordingly, this alternative door may slide vertically along the tracks from an open position to a closed position when no force is applied to the door. Alternatively, the door may comprise a plurality of slats or segments and wheels. The slats or segments may be hingedly coupled to form a unidirectionally flexible sheet, with the wheels being configured to travel along a curved pair of tracks within primary housing. The door may thus move from a closed position in a first plane to an open position in a second plane that is substantially perpendicular to the first plane, folding along a curved path like a cover on a rolltop desk or a conventional garage door. The door may be resiliently biased to the closed position and a latch mechanism may be used to selectively retain the door in the open position. Accordingly, when the latch mechanism is actuated, the door is released and the resilient member urges the door to the closed position.

In some situations it may be desired to keep the medical device within a container while inserting the insertable component into the medical device. In such a configuration, the container may further protect the sterility of the exterior of the medical device while inserting a non-sterile insertable component into the medical device. Further still, it may be useful to be able to securely close the medical device while maintaining the sterility of the exterior of a cover or cap that encloses the insertable component within the medical device. Accordingly, the following examples relate to various illustrative ways in which to secure non-sterile components within medical devices while the medical device is still within a container.

Figure 10A:
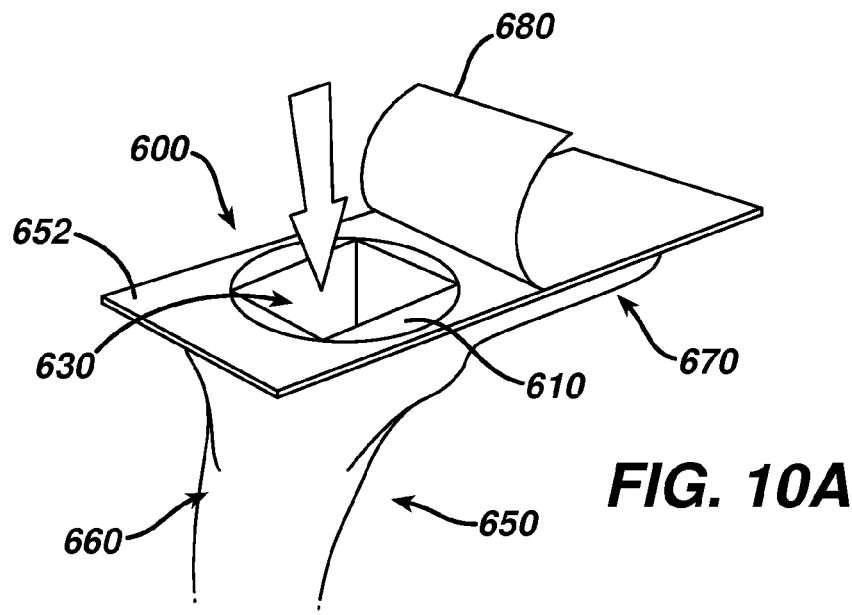
FIG. 10A depicts a perspective view of yet another exemplary feature for a medical device, utilizing a container and showing a container cover partially peeled back to expose an insertion recess.
Figure 10B:
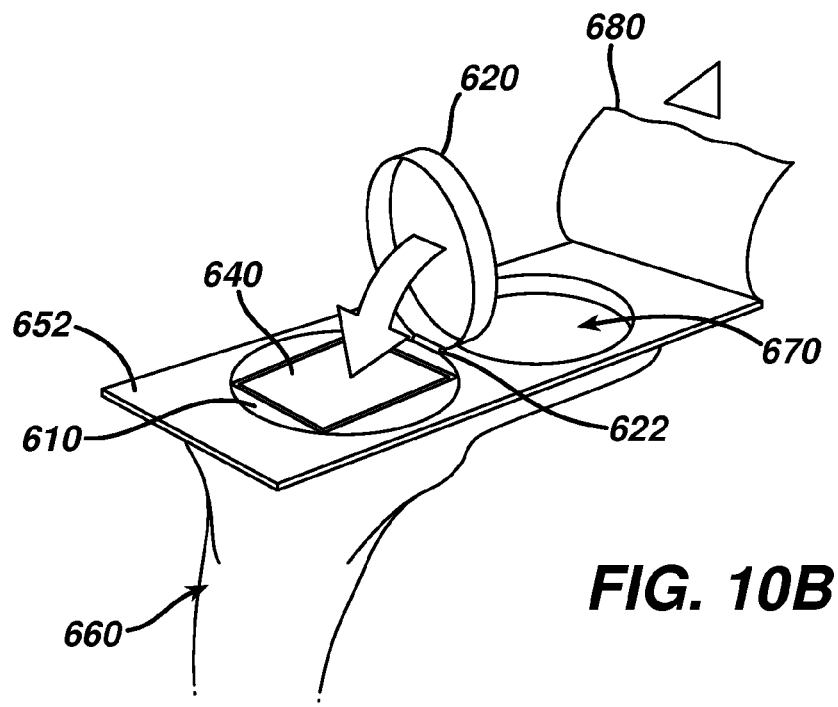
FIG. 10B depicts a perspective view of the feature of FIG. 10A, showing the container cover completely peeled back to expose a resiliently hinged cap.

FIGS. 10A-10B show an exemplary container (650) that is sized and configured to contain medical device (600). Medical device (600) may be constructed in accordance with at least some of the teachings of medical devices (10, 100), as previously discussed herein, or medical device (600) may have any other suitable configuration as will be apparent to one of ordinary skill in the art in view of the teachings herein. In the present example, medical device (600) comprises a primary housing (610) and a cap (620). Primary housing (610) comprises an insertion recess (630) sized and configured to receive an insertable component (640). By way of example only, insertable component (640) may comprise a power source, such as one of the types of batteries previously discussed herein, a plurality of batteries in the form of a battery pack, a control module, a printed circuit board, an ultrasonic transducer, and/or any other insertable component (640) or combination of components as will be apparent to those of ordinary skill in the art in view of the teachings herein.

Cap (620) is sized and configured to couple to a bottom surface of primary housing (610). In the present example, cap (620) is configured to frictionally fit to bottom surface of primary housing (610) in a closed position. Alternatively, cap (620) may further comprise a latch (not shown) to latch to a portion of primary housing (610). In yet a further example, cap (620) may comprise a resilient cantilever member (not shown) and primary housing (610) may comprise a complementary snap recess (not shown). The resilient cantilever member and snap recess may be constructed in accordance with at least some of the teachings of resilient cantilever member (430) and recess (440), as previously discussed herein, or the resilient cantilever member and snap recess may have any other suitable configuration as will be apparent to one of ordinary skill in the art in view of the teachings herein. Cap (620) may alternatively include a piece of adhesive film that may adhere to primary housing (610) to seal insertable component (640) therein. Other suitable ways in which cap (620) may be secured to primary housing (610) will be apparent to those of ordinary skill in the art in view of the teachings herein.

Cap (620) further comprises a resilient hinge (622) that hingedly attaches cap (620) to a portion of primary housing (610). Resilient hinge (622) in the present example is a spring-loaded hinge, though it should be understood that the resilient hinge (622) may have other configurations as will be apparent to those of ordinary skill in the art in light of the teachings herein. Resilient hinge (622) applies a rotational force on cap (620) to rotate cap (620) about resilient hinge (622) from an open position to the closed position. A seal (not shown) may further be attached to either cap (620) or primary housing (610) to further seal cap (620) to primary housing (610) when cap (620) is in the closed position. Both primary housing (610) and cap (620) may be made from a variety of materials including plastics, polyethylene terephthalate glycol (or PETG), thermoplastic polymer resins, or any other suitable rigid or semi-rigid material for the primary housing (610) and cap (620). While some exemplary configurations for medical device (600) have been described, various other configurations will be apparent to those of ordinary skill in the art in view of the teachings herein.

Container (650) comprises a device recess (660), a cap recess (670), a rim (652), and a container cover (680). Container (650) may be constructed in accordance with at least some of the teachings of U.S. patent application Ser. No. 13/151,515, entitled "Sterile Package System for Medical Device," filed Jun. 2, 2011, published as U.S. Pub. No. 2012/0305427 on Dec. 6, 2012, the disclosure of which is incorporated by reference herein; or container (650) may have any other suitable configuration as will be apparent to one of ordinary skill in the art in view of the teachings herein. Container (650) may be made from a variety of materials including plastics, plastic film, high density polyethylene fiber materials (such as Tyvek®), or any other suitable material to maintain sterility. In the present example, device recess (660) is sized and configured to contain primary housing (610), while cap recess (670) is sized and configured to contain cap (620) when cap (620) is in the open position. In some versions, container (650) is formed as a blister pack.

Container cover (680) is sized and configured to cover both device recess (660) and cap recess (670) when container cover (680) is coupled to container (650). Container cover (680) may be made from a variety of materials including plastics, plastic peelable film, high density polyethylene fiber materials (such as Tyvek®), or any other suitable material to maintain sterility. Container cover (680) is configured to attach to rim (652) and seal container (650). By way of example only, container cover (680) may be attached by adhesive, such as cyanoacrylate or epoxy, to rim (652) of container (650). Alternatively, container cover (680) may be configured to snap on to rim (652). In yet a further exemplary configuration, container cover (680) may be heat sealed to rim (652). Alternatively, a second container cover (not shown) may be sized and configured to cover only cap recess (670), as will be later described herein in reference to FIGS. 11A-11D. Such a second container cover may be configured to attach to a portion of rim (652) and seal cap recess (670). By way of example only, a second container cover may be attached by adhesive, such as cyanoacrylate or epoxy, to the portion of rim (652). Container cover (680) is then attached to rim (652) and seals second container cover and device recess (660). Various other materials and configurations for container (650) and container cover (680) will be apparent to those of ordinary skill in the art in view of the teachings herein.

Initially, primary housing (610) is inserted into device recess (660) and cap (620) is inserted into cap recess (670) with cap (620) being held in the open position. In the present example, container cover (680) is then coupled to rim (652) to seal cap (620) within cap recess (670) and to also seal primary housing (610) in device recess (660). Container cover (680) restrains cap (620) from being rotated by resilient hinge (622) to the closed position. Container (650) containing medical device (600) is then sterilized. In one exemplary sterilization technique, container (650) is placed in a field of radiation that can penetrate container (650), such as gamma radiation, x-rays, or high-energy electrons. The radiation may kill bacteria on primary housing (610), cap (620), and within insertion recess (630). Alternatively, container (650) may be sterilized using any other technique known in the art, including but not limited to beta or gamma radiation, ethylene oxide, electron beam sterilization, or steam. Various other suitable sterilization methods that may be provided will be apparent to those of ordinary skill in the art in view of the teachings herein.

Referring to FIG. 10A, initially a portion of container cover (680) is decoupled from rim (652) of container (650), such as by peeling container cover (680) away from container (650), to expose insertion recess (630). Insertable component (640) is then inserted into insertion recess (630). The remainder of container cover (680) is then decoupled from the remainder of rim (652) of container (650). Resilient hinge (622) then rotates cap (620) from within cap recess (670) to the closed position as shown in FIG. 10B. In the present example, if resilient hinge (622) applies a sufficient force then resilient hinge (622) may automatically frictionally fit cap (620) onto primary housing (650). Alternatively, if resilient hinge (622) does not completely frictionally fit cap (620) onto primary housing (610), the user may then manually push on cap (620) to secure cap (620) to primary housing (610) (e.g., after resilient hinge (622) has at least moved cap (620) to a position over primary housing (610), etc.). The user may then remove assembled medical device (600) from container (650) to use medical device (600) in a medical procedure.

When the user is finished with used medical device (600), cap (620) is detached from primary housing (610) (or is at least opened to reveal insertion recess (630), etc.), and insertable component (640) is then removed from insertion recess (630). A user may either manually remove insertable component (640) or the user may tip medical device (600) over to allow gravity to slide out insertable component (640). Insertable component (640) may then be reclaimed and/or recharged for reuse; or may be disposed of separately from medical device (600). Thus, a non-sterile insertable component may be inserted into and used with medical device (600) while maintaining the sterility of the exterior of medical device (600), and without exposing the insertable component to body fluids or other fluids that may contaminate the exterior of medical device (600) during use of medical device (600).

Some versions may provide closing of a cap during the process of removing a container cover from the container, without necessarily resiliently biasing the cap. FIGS. 11A-11D show a merely illustrative example of such a version, where an exemplary medical device (700) is contained within container (750). Medical device (700) may be constructed in accordance with at least some of the teachings of medical device (10), medical device (100), or medical device (600), as previously discussed herein, or medical device (700) may have any other suitable configuration as will be apparent to one of ordinary skill in the art in view of the teachings herein. In the present example, medical device (700) comprises a primary housing (710) and a cap (720). Primary housing (710) may be constructed in accordance with at least some of the teachings of primary housing (610) as described herein. Primary housing (710) comprises an insertion recess (730) sized and configured to receive an insertable component (740). By way of example only, insertable component (740) may comprise a power source, such as one of the types of batteries previously discussed herein, a plurality of batteries in the form of a battery pack, a control module, a printed circuit board, an ultrasonic transducer, and/or any other insertable component (740) or combination of components as will be apparent to those of ordinary skill in the art in view of the teachings herein.

Cap (720) may be constructed in accordance with at least some of the teachings of cap (620) as described herein. Cap (720) is sized and configured to couple to a bottom surface of primary housing (710). In the present example, cap (720) is configured to frictionally fit to bottom surface of primary housing (710) in a closed position, though other alternative suitable configurations may be provided as previously described herein. Cap (720) is coupled to primary housing (710) by a hinge (722). In one merely exemplary alternative, cap (720) may comprise a sliding door and primary housing (610) may comprise tracks on which the sliding door may slide from an open position to a closed position instead of rotating about hinge (722). Both primary housing (710) and cap (720) may be made from a variety of materials including plastics, polyethylene terephthalate glycol (or PETG), thermoplastic polymer resins, or any other suitable rigid or semi-rigid material for the primary housing (710) and cap (720).

Container (750) comprises a device recess (760), a cap recess (770), a rim (752), a first container cover (780), and a second container cover (790). Container (750) may be constructed in accordance with at least some of the teachings of container (650) or U.S. patent application Ser. No. 13/151,515, entitled "Sterile Package System for Medical Device," filed Jun. 2, 2011, published as U.S. Pub. No. 2012/0305427 on Dec. 6, 2012, the disclosure of which is incorporated by reference herein; or container (750) may have any other suitable configuration as will be apparent to one of ordinary skill in the art in view of the teachings herein. Container (750) may be made from a variety of materials including plastics, plastic film, high density polyethylene fiber materials (such as Tyvek®), or any other suitable material to maintain sterility. In the present example, device recess (760) is sized and configured to contain primary housing (710) and cap recess (770) is sized and configured to contain cap (720) when cap (720) is in the open position. In some versions, container (750) is formed as a blister pack.

First container cover (780) is sized and configured to cover both device recess (760) and cap recess (770) when coupled to container (750). Alternatively, first container cover (780) may be sized and configured to cover only device recess (760). First container cover (780) may be made from a variety of materials including plastics, plastic peelable film, high density polyethylene fiber materials (such as Tyvek®), or any other suitable material to maintain sterility. First container cover (780) is configured to attach to rim (752) to substantially seal primary housing (710) within device recess (760). By way of example only, first container cover (780) may be attached by adhesive, such as cyanoacrylate or epoxy, to rim (752) of container (750).

Second container cover (790) is sized and configured to cover only cap recess (770). In some versions, part of second container cover (790) also extends around the opening for device recess (760) yet defines an opening corresponding to the opening for device recess (760), to allow access to insertion recess (730) while second container cover (790) is still fully secured to container (750). Second container cover (790) may be made from a variety of materials including plastics, plastic peelable film, high density polyethylene fiber materials (such as Tyvek®), or any other suitable material to maintain sterility. Second container cover (790) attaches to rim (752) of container (750) and substantially seals cap (720) within cap recess (770). By way of example only, second container cover (790) may be attached by adhesive, such as cyanoacrylate or epoxy, to rim (752), though it should be understood that other suitable attachment methods may be provided as previously described herein. In the present example, container covers (780, 790) are formed as separate yet overlaid pieces. In some other versions, however, a single piece cover is used, with one portion of the single cover acting as first container cover (780) and another portion of the same single cover acting as second container cover (790). Thus, it should be understood that either container cover (780, 790) may be sized and configured to cover both cap recess (770) and device recess (760). In some such versions, a perforation, an additional line of adhesive, and/or some other feature may demarcate a boundary between recesses (760, 770), providing an interruption as the single cover is peeled from device recess (760) before the cover is peeled from cover recess (770).

Second container cover (790) of the present example further comprises a tab (792) coupled to a portion of second container cover (790) and a portion of cap (720). In the present example, tab (792) is a separate elongated flexible member having an adhesive on one side that adhesively couples to a top surface of cap (720) and to a portion of second container cover (790). Alternatively, tab (792) may be a single homogeneous continuum of material extending unitarily from second container cover (790). While a few exemplary configurations for medical device (700) and container (750) have been described, various other configurations will be apparent to those of ordinary skill in the art in view of the teachings herein.

Initially primary housing (710) is inserted into device recess (760) and cap (720) is inserted into cap recess (770). In the present example, tab (792) is coupled to cap (720) before or while cap (720) is inserted into cap recess (770). Thus, tab (792) is underneath cap (720) while cap (720) is in cap recess (770). Second container cover (790) is then attached to a portion of rim (752) to seal cap (720) within cap recess (770) First container cover (780) is then attached to rim (752) to seal primary housing (710) in device recess (760). As noted above, a single piece of film or other form of cover may be used to provide both container covers (780, 790), if desired. Container (750) containing medical device (700) is then sterilized. In one exemplary sterilization technique, container (750) is placed in a field of radiation that can penetrate container (750), such as gamma radiation, x-rays, or high-energy electrons. The radiation may kill bacteria on primary housing (710), cap (720), and within insertion recess (730). Alternatively, container (750) may be sterilized using any other technique known in the art, including but not limited to beta or gamma radiation, ethylene oxide, electron beam sterilization, or steam. Various other suitable sterilization methods that may be provided will be apparent to those of ordinary skill in the art in view of the teachings herein.

Figure 11A:
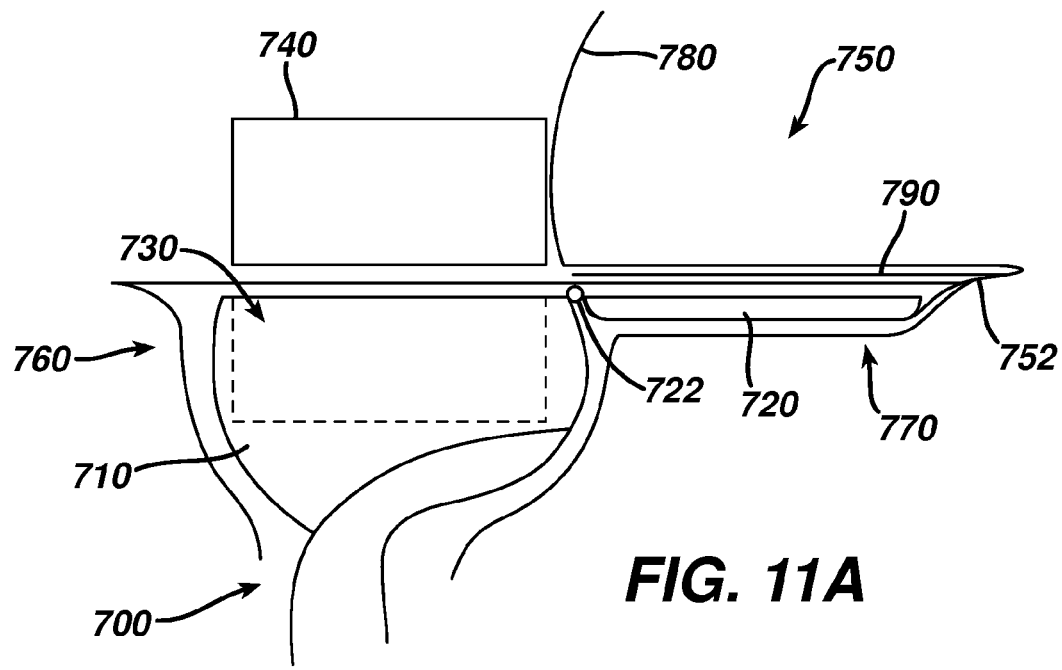
FIG. 11A depicts a side cross-sectional view of an exemplary medical device feature, incorporating a hinged cap in a container with a tab to actuate the hinged cover, showing a first container cover partially peeled away.
Figure 11B:
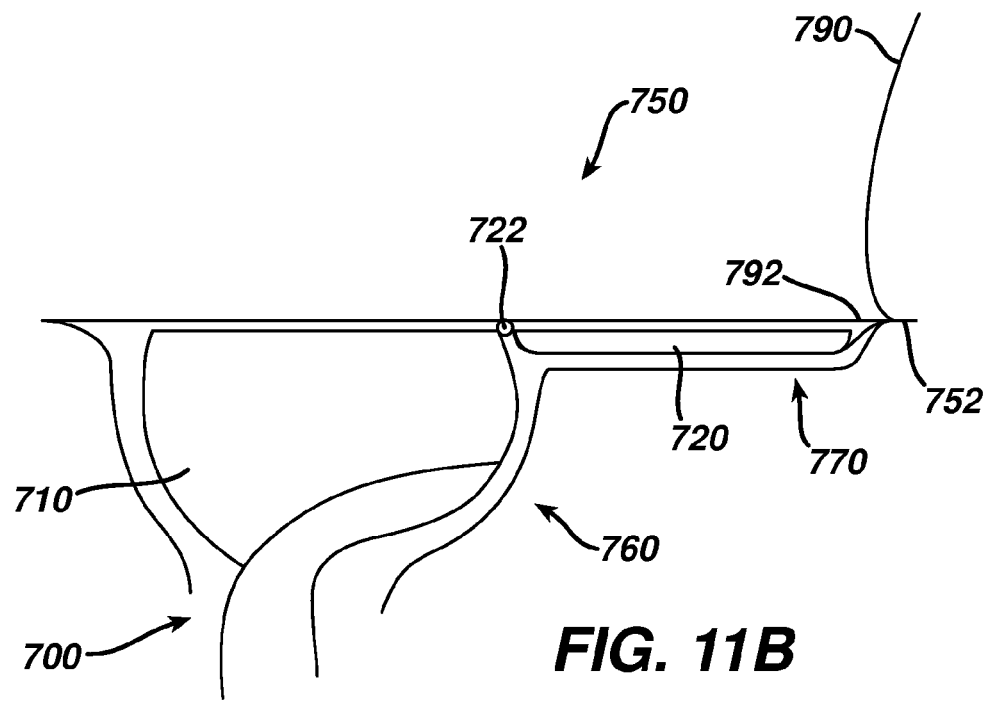
FIG. 11B depicts a side cross-sectional view of the feature of FIG. 11A, showing a second container cover peeled away.
Figure 11C:
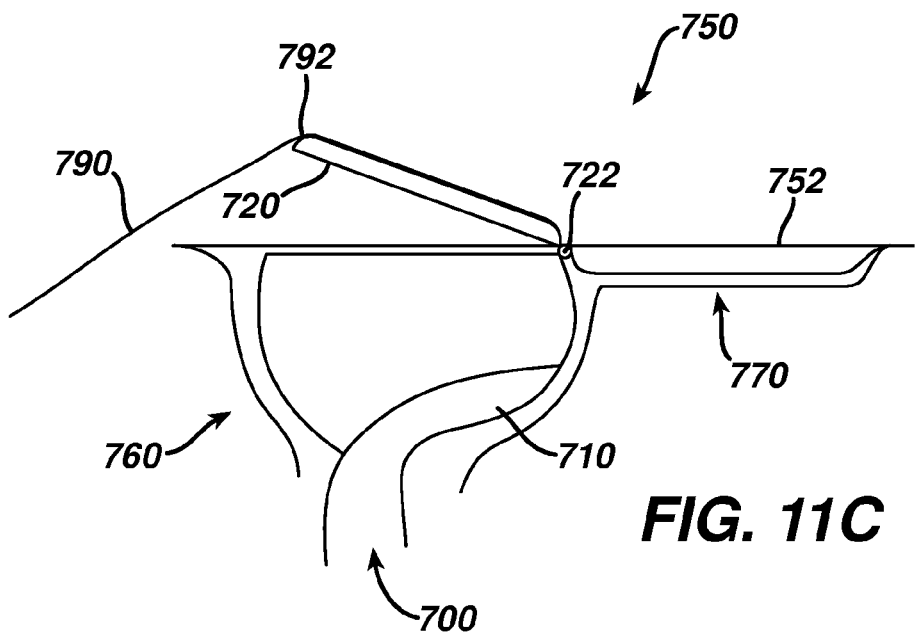
FIG. 11C depicts a side cross-sectional view of the feature of FIG. 11A, showing the second container cover and the tab pulling the cap into a closed position.
Figure 11D:
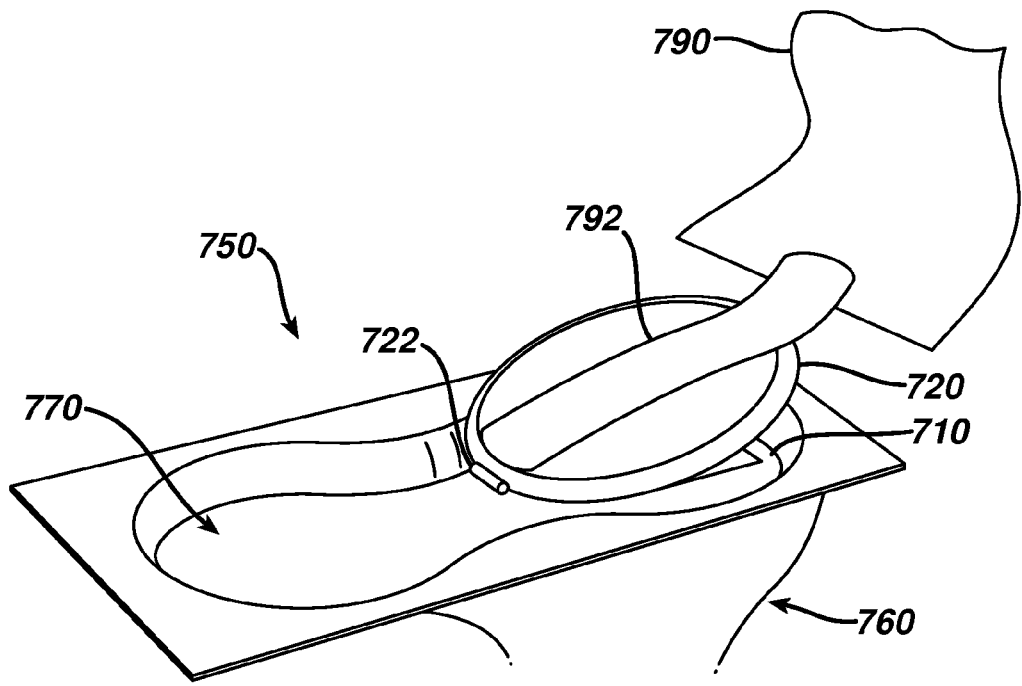
FIG. 11D depicts a perspective view of the feature as shown in FIG. 11C.

Referring to FIG. 11A, initially first container cover (780) is decoupled from rim (752) of container (750) to expose insertion recess (730) of primary housing (710). Insertable component (740) is then inserted into insertion recess (730). Insertable component (740) may be sterile or non-sterile. It should be understood that, if insertable component (740) is non-sterile, container (760) may prevent the insertion of non-sterile insertable component (740) from contaminating the sterile exterior of medical device (700). Referring to FIG. 11B, second container cover (790) is then detached from rim (752) to expose cap (720) within cap recess (770). When second container cover (790) is peeled completely off of rim (752), continued pulling on second container cover (790) transfers the force to tab (792), as seen in FIGS. 10C-10D. In particular, by pulling second container cover (790) in one direction and then back in the other direction, the user actuates cap (720) about hinge (722) to a closed position on top of primary housing (710) containing insertable component (740). In the present example, the user may then press down upon tab (792) to frictionally fit cap (720) with primary housing (710). With cap (720) secured to primary housing (710), tab (792) is then peeled off of cap (720). The user may then remove assembled medical device (700) from device recess (760) for use in a medical procedure.

When the user is finished with used medical device (700), cap (720) is detached from primary housing (710) and insertable component (740) is then removed from insertion recess (730). A user may either manually remove insertable component (740) or the user may tip medical device (700) over to allow gravity to slide out insertable component (740). Insertable component (740) may then be reclaimed and/or recharged for reuse; or be disposed of separately from medical device (700). Thus, a non-sterile insertable component may be inserted into and used with a medical device while maintaining the sterility of the exterior of the medical device; and may be further protected from body fluids or other fluids that may contact the exterior of the medical device.

In yet another exemplary alternative, an elastic member may be coupled to the cap to be stretched when the insertable component is inserted into the medical device. FIGS. 12A-12E and 13 show an exemplary medical device (800) contained within container (850). Medical device (800) may be constructed in accordance with at least some of the teachings of medical devices (10, 100, 600, 700), as previously discussed herein, or medical device (800) may have any other suitable configuration as will be apparent to one of ordinary skill in the art in view of the teachings herein. In the present example, medical device (800) comprises a primary housing (810), a cap (820), and an elastic member (824). Primary housing (810) may be constructed in accordance with at least some of the teachings of primary housing (610) as described herein. Primary housing (810) comprises an insertion recess (830) sized and configured to receive an insertable component (840).

Figure 13:
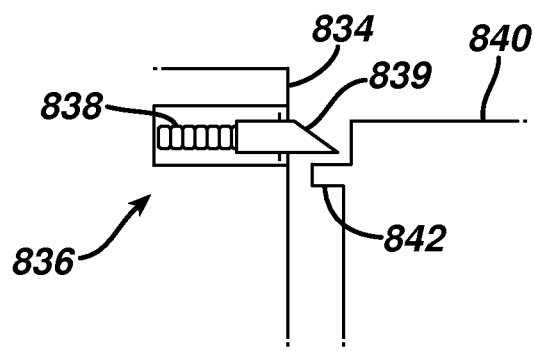
FIG. 13 depicts a partial cross-section of a latch mechanism and an insertable component protrusion for the feature of FIG. 12A.

Insertion recess (830) is defined at least in part by a base (832) and a sidewall (834). As shown in FIG. 13, sidewall (834) further comprises a retention feature (836). In the present example, retention feature (836) comprises a spring (838) coupled to a latch member (839). Retention feature (836) may further comprise a slide release (not shown) configured to couple to latch member (839). When the slide release is slid, latch member (839) compresses spring (838), thereby permitting ledge (842), described below, to pass latch member (839). By way of example only, insertable component (840) may comprise a power source, such as one of the types of batteries previously discussed herein, a plurality of batteries in the form of a battery pack, a control module, a printed circuit board, an ultrasonic transducer, and/or any other insertable component (840) or combination of components as will be apparent to those of ordinary skill in the art in view of the teachings herein. Insertable component (840) of the present example further comprises a ledge (842). When insertable component (840) is inserted into insertion recess (830), ledge (842) initially presses against latch member (839) and compresses spring (838) while ledge (842) passes latch member (839). Once insertable component (840) is fully inserted into insertion recess (830), ledge (842) passes below latch member (839) and spring (838) decompresses to return latch member (839) to a fully extended position as seen in FIG. 13, such that latch member (839) thereafter retains insertable component (840) within insertion recess (830).

Cap (820) may be constructed in accordance with at least some of the teachings of cap (620) as described herein. Cap (820) is sized and configured to couple to a bottom surface of primary housing (810). In the present example, cap (820) is configured to frictionally fit to bottom surface of primary housing (810) in a closed position, though other alternative suitable configurations may be provided as previously described herein. Cap (820) is coupled to primary housing (810) by a hinge (822). Both primary housing (810) and cap (820) may be made from a variety of materials including plastics, polyethylene terephthalate glycol (or PETG), thermoplastic polymer resins, or any other suitable rigid or semi-rigid material for the primary housing (810) and cap (820).

In the present example, elastic member (824) is coupled to an interior portion of cap (820) and to base (832) of insertion recess (830). When cap (820) is in an open position, elastic member (824) is in a taut, but not stretched position. When insertable component (840) is inserted into insertion recess (830), insertable component (840) stretches elastic member (824) to a stretched position. With insertable component (840) secured within insertion recess (830) by latch member (839), elastic member (824) pulls on cap (820) to actuate cap (820) about hinge (822) from the open position to the closed position. In the present example, elastic member (824) is a rubber band, though it should be understood that other elastomeric materials may be utilized, including silicone rubbers, fluoroelastomers, ethylene propylene diene rubber (EPDM), nitrile rubbers, styrene-butadiene rubber, butyl rubber, chloroprene, polychloroprene, polybutadiene rubber, isoprene rubber, India rubber, and/or any other suitable elastomeric material or combinations of elastomeric materials as will be apparent to one of ordinary skill in the art in view of the teachings herein. It should also be understood that elastic member (824) need not necessarily elastic. For instance, a flexible yet inelastic strip of material in place of elastic member (824) may still pull cap (820) closed upon insertion of insertable component (840) into insertion recess (830). In some such versions, container (850) has only one cover (e.g., a single peelable film cover) instead of having two covers (880, 890) as described below.

Container (850) of this example comprises a device recess (860), a cap recess (870), a rim (852), a first container cover (880), and a second container cover (890). Container (850) may be constructed in accordance with at least some of the teachings of container (650), container (750), or U.S. patent application Ser. No. 13/151,515, entitled "Sterile Package System for Medical Device," filed Jun. 2, 2011, published as U.S. Pub. No. 2012/0305427 on Dec. 6, 2012, the disclosure of which is incorporated by reference herein; or container (850) may have any other suitable configuration as will be apparent to one of ordinary skill in the art in view of the teachings herein. Container (850) may be made from a variety of materials including plastics, plastic film, high density polyethylene fiber materials (such as Tyvek®), or any other suitable material to maintain sterility. In the present example, device recess (860) is sized and configured to contain primary housing (810) and cap recess (870) is sized and configured to contain cap (820) when cap (820) is in the open position. In some versions, exemplary container (850) is formed as a blister pack.

First container cover (880) of the present example is sized and configured to cover both device recess (860) and cap recess (870) when coupled to container (850). Alternatively, first container cover (880) may be sized and configured to cover only device recess (860). First container cover (880) may be made from a variety of materials including plastics, plastic peelable film, high density polyethylene fiber materials (such as Tyvek®), or any other suitable material to maintain sterility. First container cover (880) is configured to attach to rim (852) to substantially seal primary housing (810) within device recess (860). By way of example only, first container cover (880) may be attached by adhesive, such as cyanoacrylate or epoxy, to rim (852) of container (850).

Second container cover (890) is sized and configured to cover only cap recess (870). Second container cover (890) may be made from a variety of materials including plastics, plastic peelable film, high density polyethylene fiber materials (such as Tyvek®), or any other suitable material to maintain sterility. Second container cover (890) attaches to rim (852) of container (850) and substantially seals cap (820) within cap recess (870). By way of example only, second container cover (890) may be attached by adhesive, such as cyanoacrylate or epoxy, to rim (852), though it should be understood that other suitable attachment methods may be provided as previously described herein. It should also be understood that a single piece of film or a single cap, etc., may serve as both first and second container covers (880, 890), as described above with respect to container covers (780, 790) or otherwise. While a few exemplary configurations for medical device (800) and container (850) have been described, various other configurations will be apparent to those of ordinary skill in the art in view of the teachings herein.

Initially primary housing (810) is inserted into device recess (860) and cap (820) is rotatably inserted into cap recess (870) about hinge (822). In the present example, when cap (820) is in the open position, elastic member (824) is taut. Second container cover (890) is then attached to a portion of rim (852) to seal cap (820) within cap recess (870). First container cover (880) is then attached to rim (852) to seal primary housing (810) in device recess (860). As noted above, a single piece of film or other form of cover may be used to provide both container covers (880, 890), if desired. Container (850) containing medical device (800) is then sterilized. In one exemplary sterilization technique, container (850) is placed in a field of radiation that can penetrate container (850), such as gamma radiation, x-rays, or high-energy electrons. The radiation may kill bacteria on primary housing (810), cap (820), elastic member (824), and within insertion recess (830). Alternatively, container (850) may be sterilized using any other technique known in the art, including but not limited to beta or gamma radiation, ethylene oxide, electron beam sterilization, or steam. Various other suitable sterilization methods that may be provided will be apparent to those of ordinary skill in the art in view of the teachings herein.

Figure 12A:
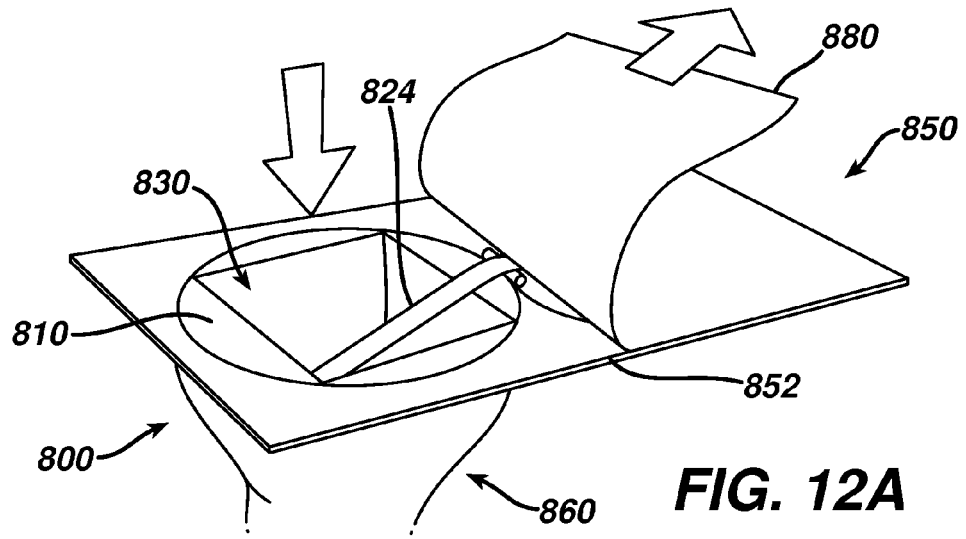
FIG. 12A depicts a perspective view of yet another exemplary alternative medical device feature, incorporating an elastic member.
Figure 12B:
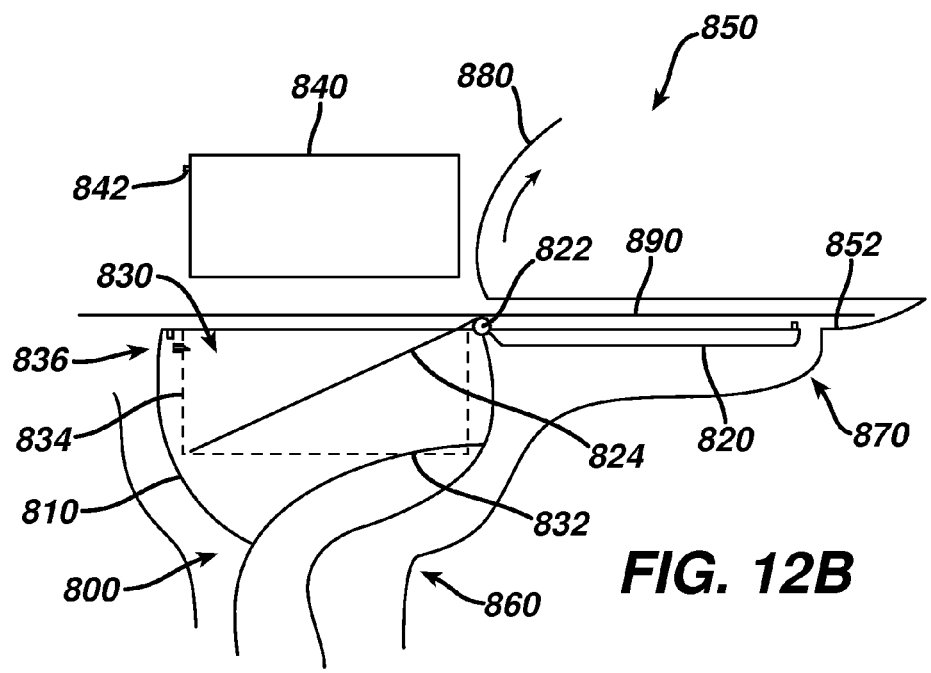
FIG. 12B depicts a side cross-sectional view of the feature of FIG. 12A, showing a first container cover partially peeled away prior to the insertion of an insertable component.
Figure 12C:
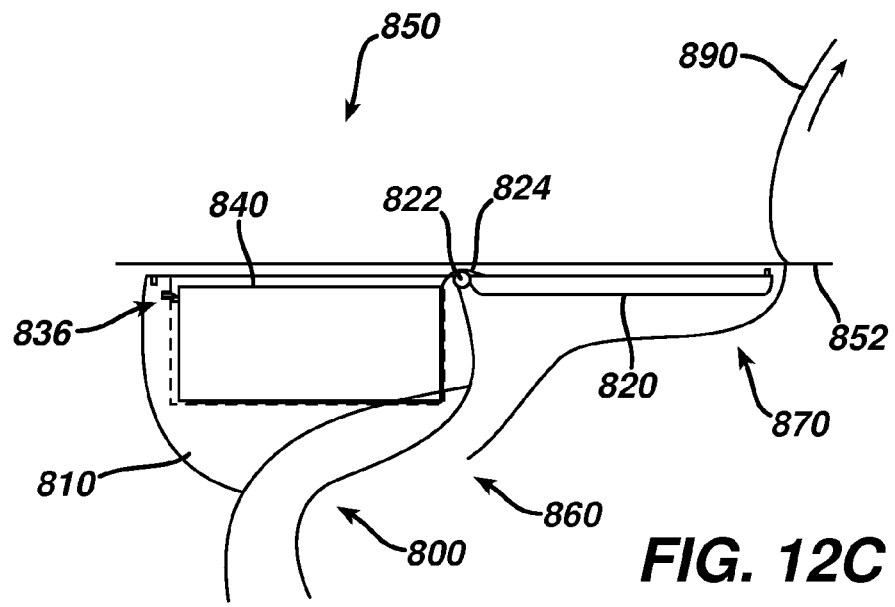
FIG. 12C depicts a side cross-sectional view of the feature of FIG. 12A, showing the insertable component inserted into an insertion recess and the elastic member in a stretched position.
Figure 12D:
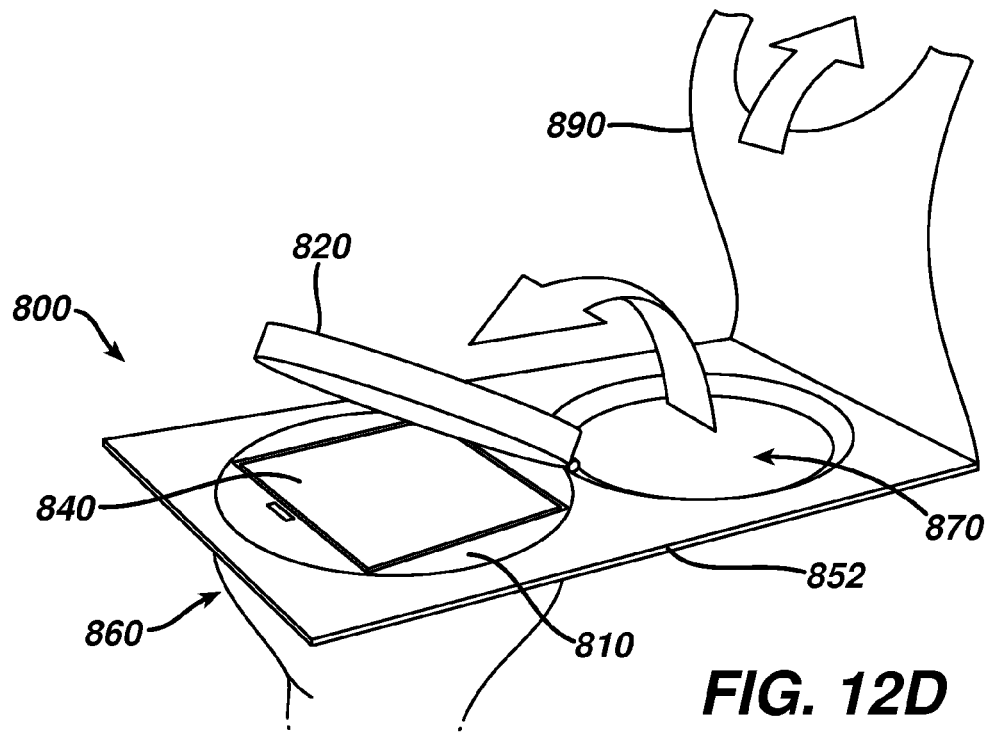
FIG. 12D depicts a perspective view of the feature of FIG. 12A, showing the cap actuating into a closed position.
Figure 12E:
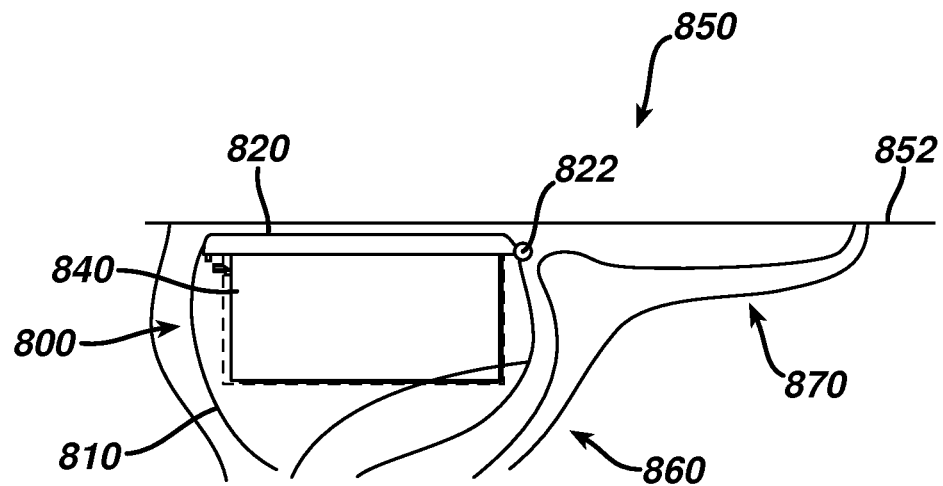
FIG. 12E depicts a side cross-sectional view of the feature of FIG. 12A, showing the cap in the closed position.

Referring to FIG. 12A, initially first container cover (880) is decoupled from rim (852) of container (850) to expose insertion recess (830) of primary housing (810). Insertable component (840) is then inserted into insertion recess (830), as shown in FIG. 12B. When insertable component (840) is inserted into insertion recess (830), ledge (842) initially presses against latch member (839) and compresses spring (838) while ledge (842) passes latch member (839). Once insertable component (840) is fully inserted into insertion recess (830), ledge (842) passes below latch member (839) and spring (838) decompresses to return latch member (839) to a fully extended position, as seen in FIG. 13. With insertable component (840) inserted in insertion recess (830), elastic member (824) is in a stretched position, as depicted in FIG. 12C. Second container cover (890) is then detached from rim (852) to expose cap (820) within cap recess (870). When second container cover (890) is peeled completely off of rim (852), elastic member (824) in the stretched position pulls upon cap (820) to rotate cap (820) about hinge (822) from the open position to the closed position, as seen in FIGS. 12C-12E. In the present example, if cap (820) does not automatically secure itself to primary housing (810), then the user may then press down upon cap (820) to frictionally fit cap (820) to primary housing (810). With cap (820) secured to primary housing (810), the user may then remove assembled medical device (800) for use in a medical procedure.

When the user is finished with used medical device (800), cap (820) is detached from primary housing (810). Cap (820)

may be held in the open position manually by a user or cap (820) may be held open by some other means, such as reclamation container cover. With cap (820) held open, elastic member (824) is stretched into the stretched position again. In some versions where a flexible yet inelastic piece of material is used instead of elastic member (824), opening of cap (820) with insertable component (840) in medical device (800) may snap or tear the flexible yet inelastic piece of material. In the present example, stretched elastic member (824) applies a force to insertable component (840), which in turn pushes ledge (842) against latch member (839). When latch member (839) is moved to compress spring (838), either directly or by a slide release, ledge (842) is no longer restrained by latch member (839) and insertable component (840) may "pop out" of insertion recess (830) due to the bias provided by elastic member (824). If insertable component (840) does not completely exit insertion recess (830), a user may either manually remove insertable component (840) or the user may tip medical device (800) over to allow gravity to slide out insertable component (840). Insertable component (840) may then be reclaimed and/or recharged for reuse; or be disposed of separately from medical device (800). Thus, a non-sterile insertable component may be inserted into and used with a medical device while maintaining the sterility of the exterior of the medical device; and may be further protected from body fluids or other fluids that may contact the exterior of the medical device.

While various configurations for medical devices (500, 600, 700, 800) with insertable component features have been described, various other suitable configurations will be apparent to those of ordinary skill in the art in view of the teachings herein.

D. Alternative Closure Mechanisms for Medical Devices

In some situations it may be desired to mechanically couple an insertable component while inserting the insertable component into the medical device. In some such situations an insertion member, a cap, or a feature of the medical device may facilitate the coupling of the insertable component within the device. The following examples relate to various configurations for inserting an insertable component into a medical device and mechanically securing the insertable component therein, while several other examples will be apparent to those of ordinary skill in the art in view of the teachings herein.

FIGS. 14A-14D and 15 depict an exemplary configuration implementing an insertion assembly (900) with a medical device (950) having a sterile flexible member (980). Medical device (950) may be constructed in accordance with at least some of the teachings of medical devices (10, 100), as previously discussed herein, or medical device (950) may have any other suitable configuration as will be apparent to one of ordinary skill in the art in view of the teachings herein. In the present example, medical device (950) comprises a primary housing (960), an insertion recess (970) located on a portion of primary housing (960), and sterile flexible member (980). Primary housing (960) may be made from a variety of materials including plastics, polyethylene terephthalate glycol (or PETG), thermoplastic polymer resins, or any other suitable rigid or semi-rigid material for the primary housing (960). In the present example, insertion recess (970) is located on a proximal end (962) of primary housing (960). Insertion recess (970) is also sized and configured to receive an insertable component (940) within insertion recess (970). By way of example only, insertable component (940) may comprise a power source, such as one of the types of batteries previously discussed herein, a plurality of batteries in the form of a battery pack, a control module, a printed circuit board, an ultrasonic transducer, and/or any other insertable component (940) or combination of components as will be apparent to those of ordinary skill in the art in view of the teachings herein. Insertion recess (970) is shown in FIG. 15 as a cylindrical recess within primary housing (960), though any other suitable shape may be used. Insertion recess (970) further comprises a locking portion (972) configured to receive a portion of insertable component (940). In the present example, locking portion (972) is a rectangular recess within insertion recess (970), though it should be understood that this is merely optional. Other suitable configurations for locking portion (972) may include various geometrically shaped recesses, such as stars, squares, or other polygons; or locking portion (972) may be a protrusion that inserts into a portion of insertable component (940).

Sterile flexible member (980) of the present example comprises a folded piece of material that forms a tubular portion extending from the proximal end (962) of primary housing (960). In the present example sterile flexible member (980) is shown attached by its distal end to the exterior of primary housing (960), though it should be understood that this is merely optional. Sterile flexible member (980) may be integrated with a portion of primary housing (960) or sterile flexible member (980) may be contained within a slot (not shown) formed in primary housing (960). In the present example, sterile flexible member (980) forms a flexible sock. Other suitable materials for sterile flexible member (980) include neoprene, nitrile rubber, silicone rubbers, fluoroelastomers, ethylene propylene diene rubber (EPDM), cloth, malleable plastics, or any other suitable flexible material as will be apparent to one of ordinary skill in the art in light of the teachings herein. Sterile flexible member (980) further comprises an end member (982), though it should be understood that this component is merely optional. End member (982) of the present example includes a weighted portion coupled to sterile flexible member (980) at a proximal end opposite the distal end. End member (982) may thus keep sterile flexible member in a folded over position by the weight of end member (982). In addition or in the alternative, end member (982) may comprise a circular elastomeric member, such as a rubber band, o-ring, or elastic band. In this configuration, when insertion tube (990) is inserted into sterile flexible member (980), the elastic end member (982) stretches around insertion tube (990) and retains insertion tube (990) within sterile flexible member by friction. Furthermore, when insertion tube (990) is removed, the elastic end member (982) may be sized to substantially close the proximal end of sterile flexible member (980) when the elastic end member (982) returns to a relaxed position. In yet a further configuration, end member (982) may comprise a circular rigid member sized to tightly fit insertion tube (990) therein. Further configurations for end member (982) will be apparent to one of ordinary skill in the art in view of the teachings herein.

Insertion tube (990) of the present example comprises a cylindrical member with an inner diameter at least equal to the diameter of insertion recess (970) and is sized to permit insertable component (940) to be inserted therethrough. It should be understood that insertion tube (990) may comprise other alternative geometric cross-sections, including rectangles, squares, triangles, or any other polygon that is suitable to permit insertable component (940) be inserted through insertion tube (990) and into insertion recess (970). In the present example, insertion tube (990) is a rigid member insertable into sterile flexible member (980), though it should be understood that insertion tube (990) may comprise a semi-rigid or flexible member as well. In the present example, rigid insertion tube (990) may be made from plastics, polyethylene terephthalate glycol (or PETG), thermoplastic polymer resins, or any other suitable rigid material as will be apparent to one of ordinary skill in the art in view of the teachings herein.

Insertion assembly (900) comprises insertable component (940) coupled to a handle (910). By way of example only, a handle (910) may further comprise an attachment portion (920) and a grip portion (930). Attachment portion is configured to rigidly yet removably attach to a proximal end of insertable component (940). Exemplary attachments include by adhesives, such as cyanoacrylate, epoxy, or thermoplastics, by integral formation with an exterior portion of insertable component (940), or by any other suitable attachment as will be apparent to those of ordinary skill in the art in light of the teachings herein. Grip portion (930) is configured to be gripped by a user. In particular, grip portion (930) may include ridges or other grip-aiding formations to assist a user to grasp grip portion (930). This may be particularly useful if the user is wearing medical gloves while using insertion assembly (900). Insertable component (940) may further comprise a retrieval portion (not shown) such as a separate notch or recess in the proximal end of insertable component (940) such that a separate retrieval handle (not shown) may be used to remove insertable component (940) after use of medical device (950). The notch or recess may permit insertable component (940) to be turned to decouple insertable component (940) from locking portion (972) after use.

A separate closure member (984) is also provided for use after insertable component (940) is inserted into medical device (950). Closure member (984) is sized and configured to substantially seal sterile flexible member (980) together to encase insertable component (940) within sterile flexible member (984). Closure member (984) in the present example is an elastomeric member (such as a rubber band, o-ring, or elastic band) that fits around sterile flexible member (980) and compresses the folded portions of sterile flexible member (980) together. Alternatively, closure member (984) may comprise a draw string, a clothespin, clip, clamp, or other separable mechanical closure mechanism. Further still, closure member (984) may be integrated within sterile flexible member (984). Exemplary closure members in this configuration include zip-lock closures, adhesive patches, adhesive gum, thermoplastic or heat sealing members, pressure adhesives, buttons, zippers, snap fasteners, or any other suitable closure member as will be apparent to one of ordinary skill in the art in view of the teachings herein.

Initially, medical device (950), comprising primary housing (960) and sterile flexible member (980), is sterilized. In one exemplary sterilization technique, medical device (950) is placed in a field of radiation that can penetrate medical device (950), such as gamma radiation, x-rays, or high-energy electrons. The radiation may kill bacteria on primary housing (960), sterile flexible member (980), and within insertion recess (970). Alternatively, medical device (950) may be sterilized using any other technique known in the art, including but not limited to beta or gamma radiation, ethylene oxide, electron beam sterilization, or steam. In another alternative, insertion tube (990) may be inserted into sterile flexible member (980) prior to sterilization and insertion tube (990) may also be sterilized when medical device (950) is sterilized. Various other suitable sterilization methods that may be provided will be apparent to those of ordinary skill in the art in view of the teachings herein.

When a user wants to use medical device (950), the user initially inserts insertion tube (990) into sterile flexible member (980) if this has not been previously done. The user then grasps insertion assembly (900) by grip portion (930) and guides insertable component (940) through insertion tube (990) and into insertion recess (970), as shown in FIG. 14A. If insertable component (940) is non-sterile, insertion tube (990) protects sterile flexible member (980) from contamination by the non-sterile insertable component (940). Once insertable component (940) is within insertion recess (970), a portion of insertable component (940) is aligned with and inserted into locking portion (972). This may include an electrical connection (such as a contact on a battery or circuit board, etc.) or physical connection (such as threading, snap-fitting, etc.) for insertable component (940). As shown in FIG. 14B, once inserted into the locking portion (972), the user rotates handle (910) by grip portion (930) to detach attachment portion (920) from insertable component (940). In the present example, when the portion of insertable component (940) is inserted into locking portion (972) of insertion recess (970), the user may rotate handle (910) is any direction to detach attachment portion (920) from insertable component (940). Alternatively, if insertable component (940) is coupled by a threaded attachment, then the user continues to rotate handle in the direction to tighten insertable component (940) with the threads until attachment portion (920) detaches.

Once handle (910) is detached from insertable component (940), handle (910) may be removed and stored for reuse, if possible, or disposed of. With insertable component (940) contained within insertion recess (970), insertion tube (990) is removed from within sterile flexible member (980), as shown in FIG. 14C. Closure member (984) of the present example (such as a rubber band or o-ring) is then placed around sterile flexible member (980) and cinches together the folded portions of sterile flexible member (980), thereby substantially sealing insertable component (940) within medical device (950), as shown in FIG. 14D. Thus, with the aid of insertion tube (990) and insertion assembly (900), a non-sterile insertable component (940) may be inserted into medical device (950) without substantially contaminating medical device (950). The user may then use medical device (950) for a medical operation.

To remove insertable component (940), closure member (984) is initially removed from sterile flexible member (980). Sterile flexible member (980) is then opened and insertable component (940) may then be manually removed or slide out of sterile flexible member (980) by gravity. If insertable component (940) is coupled to locking portion (972) a separate retrieval handle (not shown) may couple to a retrieval portion (not shown) to turn insertable component (940) and decouple insertable component (940) from locking portion (972). Alternatively, handle (910) may be configured to assist with removal of insertable component (940) from locking portion (972). After being removed from medical device (950), insertable component (940) may be reclaimed and/or recharged for reuse; or be disposed of separately from medical device (950). Thus, a non-sterile insertable component may be inserted into and used with a medical device while maintaining the sterility of the exterior of the medical device; and may be further protected from body fluids or other fluids that may contact the exterior of the medical device.

Figure 16:
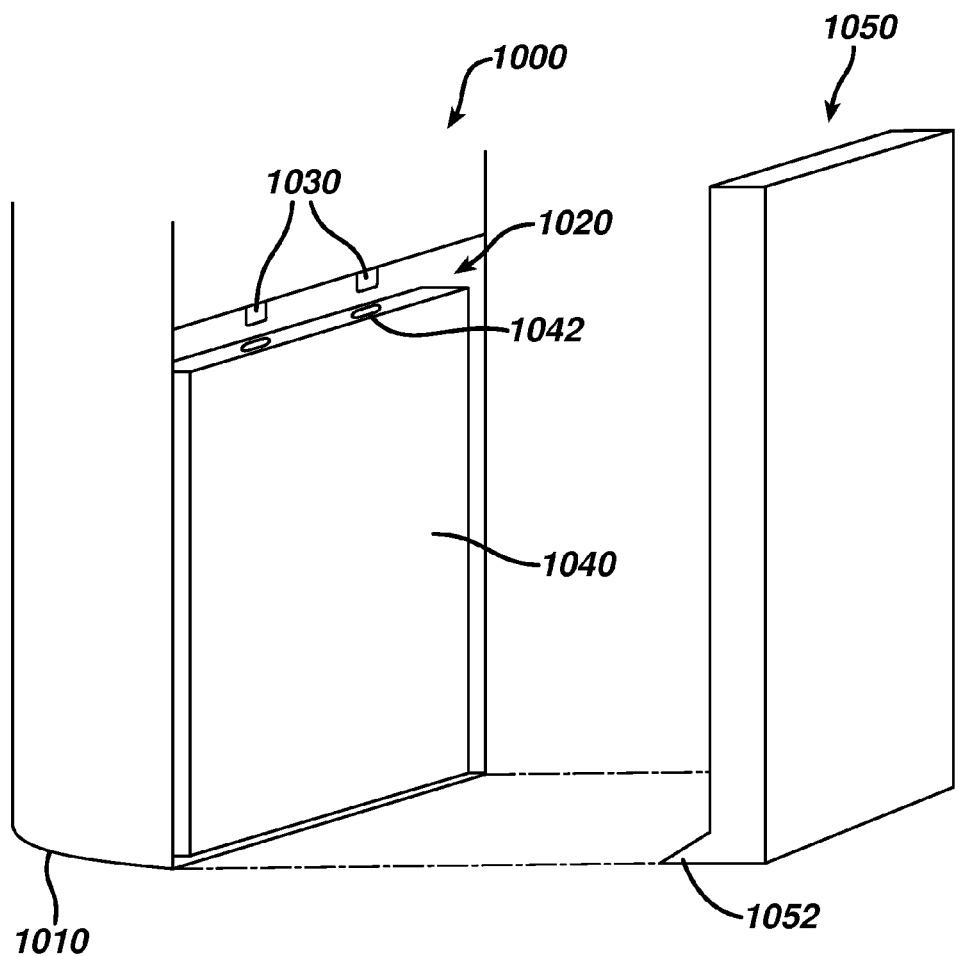
FIG. 16 depicts a perspective view of an exemplary feature for an insertable component in a medical device, incorporating a zero-insertion-force mechanism.

In yet a further configuration it may be useful to have a zero-insertion-force (ZIF) mechanism for coupling the insertable component within the medical device. In some such configurations, a non-sterile user inserts a non-sterile insertable component into a recess within the device (using virtually no insertion force), and then a sterile user couples a cover to the medical device to thereby fully couple the insertable component within the device. One merely illustrative example of such a medical device (1000) is shown in FIG. 16. Medical device (1000) of this example may be constructed in accordance with at least some of the teachings of medical devices (10, 100), as previously discussed herein, or medical device (1000) may have any other suitable configuration as will be apparent to one of ordinary skill in the art in view of the teachings herein. In the present example, medical device (1000) comprises a primary housing (1010), an insertion recess (1020) located in a portion of primary housing (1010), and connections (1030) located within insertion recess (1020). Primary housing (1010) may be made from a variety of materials including plastics, polyethylene terephthalate glycol (or PETG), thermoplastic polymer resins, or any other suitable rigid or semi-rigid material for the primary housing (1010).

Insertion recess (1020) of the present example is located on a rear surface of primary housing (1010). Electrical connections (1030) extend from an inner surface of insertion recess (1020). In the present example, connections (1030) extend from the top surface of insertion recess (1020), though it should be understood that connections (1030) may be located on any surface of insertion recess (1020). Insertion recess (1020) is sized slightly larger than an insertable component (1040) such that when insertable component (1040) is inserted into insertion recess (1020), connections (1030) do not couple with component connections (1042), and nothing provides mechanical resistance against insertion of insertable component (1040) in insertion recess (1020). Insertable component (1040) comprises component connections (1042) located on a surface corresponding to connections (1030) when insertable component (1040) is inserted within insertion recess (1020). By way of example only, insertable component (1040) may comprise a power source, such as one of the types of batteries previously discussed herein, a plurality of batteries in the form of a battery pack, a control module, a printed circuit board, an ultrasonic transducer, and/or any other insertable component (1040) or combination of components as will be apparent to those of ordinary skill in the art in view of the teachings herein. In the present example, insertable component (1040) comprises a battery pack having two electrical component connections (1042) on a top surface of insertable component (1040). The component connections (1042) of the present example are configured to electrically couple to connections (1030) once cap (1050) is coupled to primary housing (1010).

Cap (1050) is sized and configured to couple to primary housing (1010) to seal insertable component (1040) therein. Cap (1050) may be constructed in accordance with at least some of the teachings of cover (420), as previously discussed herein, or cap (1050) may have any other suitable configuration as will be apparent to one of ordinary skill in the art in view of the teachings herein. Some merely exemplary features of cover (420) that may be readily incorporated into cap (1050) include resilient cantilever members (430). If resilient cantilever members (430) are included, primary housing (1010) may further comprise complementary recesses configured in accordance with at least some of the teachings of recesses (440) described above. Cap (1050) of the present example further comprises an angled ledge (1052). Angled ledge (1052) is sized such that when cap (1050) is coupled with primary housing (1010), angled ledge (1052) cams insertable component (1040) upwards within insertion recess (1020) to connect component connection (1042) to connections (1030). Cap (1050) may be made from a variety of materials including plastics, polyethylene terephthalate glycol (or PETG), thermoplastic polymer resins, or any other suitable rigid or semi-rigid material for the cap (1050). Angled ledge (1052) may be formed as a single homogeneous continuum of material extending from cap (1050), or angled ledge (1052) may be a separable component that is mechanically attached to cap (1050).

Cap (1050) may further comprise a protrusion (not shown) that is located on a plane parallel to connections (1030). The protrusion may be a semi-rigid protrusion with openings sized to permit connections (1030) to extend therethrough. A top surface of the protrusion may further comprise an abrasive material, such as sand paper, a fine grit, rigid metal bristles, etc. When cap (1050) is coupled to primary housing (1010), the abrasive material wipes against connections (1030) to increase the electrical conductivity. Connections (1030) then extend through the openings of the protrusion to couple to component connections (1042). In yet another alternative, a pull tab (not shown) may be adhesively attached to connections (1030) or component connections (1042). The pull tab may be sized such that a first portion extends out of insertion recess (1020) after cover (1050) is attached. A second portion may extend in an opposite direction of the first portion and may further comprise an abrasive material. When cap (1050) is coupled to primary housing (1010), the pull tabs may prevent connections (1030) from coupling with component connections (1042). The pull tab may then be pulled, wiping the abrasive second portion across connections (1030) or component connections (1042). After the pull tab is removed, connections (1030) couple to component connections (1042). Of course, such abrasive features are merely optional.

Figure 17:
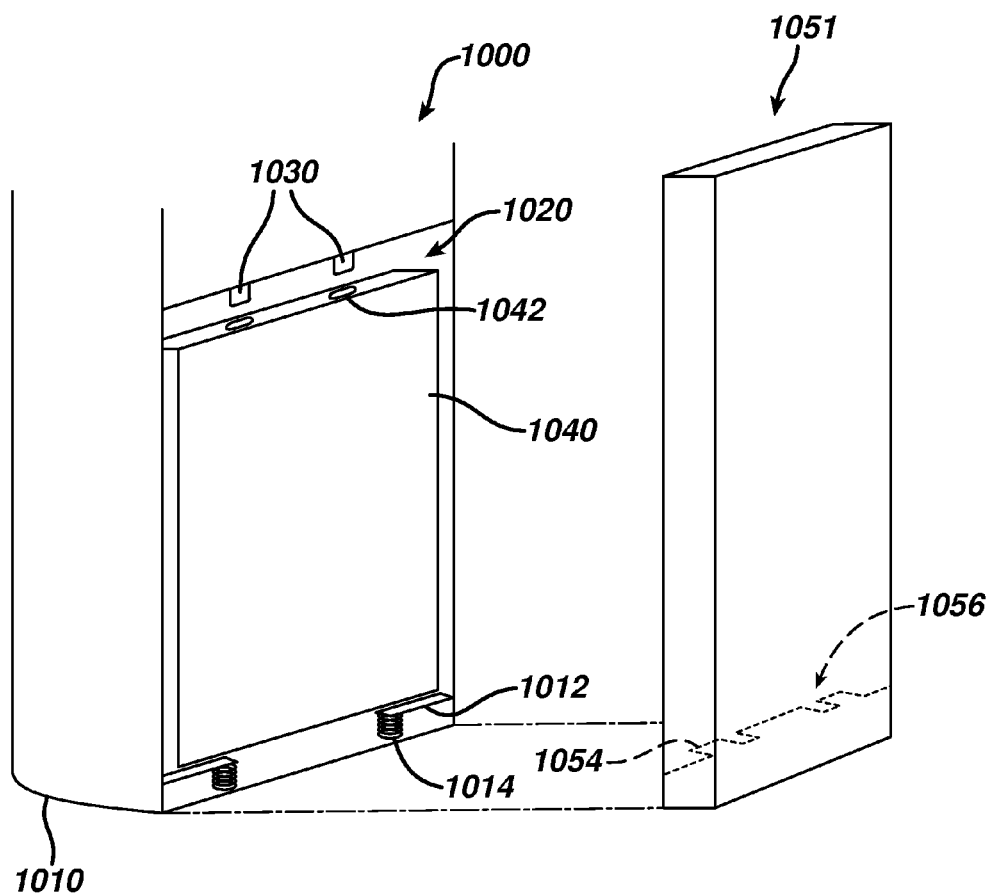
FIG. 17 depicts a perspective view of an exemplary alternative feature for an insertable component in a medical device, incorporating a zero-insertion-force mechanism.

In an exemplary alternative configuration, as shown in FIG. 17, primary housing (1010) may further comprise rotating members (1012) and springs (1014). In an initial state, rotating members (1012) restrain springs (1014) in a compressed state. Cap (1051) of this example comprises a ledge (1054) comprising notches (1056) that correspond to the location of springs (1014). In this configuration, when cap (1051) is coupled to primary housing (1010) with insertable component (1040) contained therein, ledge (1054) pushes on and rotates rotating members (1012). Once rotating members (1012) are clear of springs (1014), springs (1014) decompress and extend through notches (1056). Springs (1014) push insertable component (1040) upwards within insertion recess (1020) to couple component connections (1042) to connections (1030).

In yet another exemplary configuration, primary housing (1010) may comprise tracks (not shown) extending vertically on the exterior of primary housing (1010). An alternative cap (not shown) may have corresponding protrusions that fit into the tracks and guide the cap to slidably couple with primary housing (1010). Primary housing (1010) may further comprise an opening or openings at the base of insertion recess (1020). The alternative cap may then comprise a corresponding protrusion (not shown) to push upon the bottom of insertable component (1040) when the cap is slid onto primary housing (1010). Thus, when the cap is coupled to primary housing (1010), the protrusion pushes insertable component (1040) upwards to couple component connections (1042) with connections (1030). It should be understood that a spring, or pair of springs, may be readily interchangeable with the protrusion of this alternative cap.

It should be understood from the foregoing that a non-sterile insertable component (1040) may be readily inserted into a medical device (1010) without compromising the sterility of the exterior of medical device (1010); and may further be secured and sealed within medical device (1010) by a cap (1050, 1051). When the user is finished with medical device (1000), cap (1050, 1051) is removed and insertable component (1040) may simply be dropped out of insertion recess (1040) for recharging, reclamation, and/or any other purpose. Thus, in the foregoing exemplary configurations a non-sterile insertable component may be inserted into a medical device and subsequently coupled when a cap is attached to the medical device. The low force required by the exemplary ZIF connections permit a user to seal the medical device while limiting the potential for contamination from the non-sterile component contained therein. Furthermore, caps (1050, 1051) may protect insertable component (1040) from coming into contact with body fluids and/or other fluids encountered by medical device (1010) during use of medical device (1010).

While various configurations for medical device (1000) and cap (1050, 1051) have been described, various other configurations may be provided as will be apparent to those of ordinary skill in the art in view of the teachings herein.

It may also be desired in some settings for an integral feature of a medical device to provide insertion of an insertable component within the medical device. FIGS. 18, 19, and 20A-20B depict some examples of such integral features, while still other examples will be apparent to those of ordinary skill in the art in view of the teachings herein.

The medical device (1100) shown in FIGS. 18-19 may be constructed in accordance with at least some of the teachings of medical devices (10, 100), as previously discussed herein, or medical device (1100) may have any other suitable configuration as will be apparent to one of ordinary skill in the art in view of the teachings herein. In the present example, medical device (1100) comprises a primary housing (1110) having an insertion recess (1120) configured to accommodate an insertable component (1150). By way of example only, insertable component (1150) may comprise a power source, such as one of the types of batteries previously discussed herein, a plurality of batteries in the form of a battery pack, a control module, a printed circuit board, an ultrasonic transducer, and/or any other insertable component (1150) or combination of components as will be apparent to those of ordinary skill in the art in view of the teachings herein. Primary housing (1110) may be made from a variety of materials including plastics, polyethylene terephthalate glycol (or PETG), thermoplastic polymer resins, or any other suitable rigid or semi-rigid material for the primary housing (1110).

Primary housing (1110) of the present example further comprises a pair of tracks (1130) and a lift assembly (1140). Tracks (1130) of the present example comprise vertical grooves within the interior of primary housing (1110). Exemplary tracks (1130) are further sized to fit a pair of complementary protrusions (1146) of lift assembly (1140), as will be discussed below. In one alternative, tracks (1130) may comprise a groove portion and a plurality of ball bearings contained within the groove portion to assist in the smooth sliding of protrusions (1146) along tracks (1130). In yet another alternative, tracks (1130) may comprise C-channel portions to accommodate a pair of wheels within tracks (1130). Yet other suitable configurations for tracks (1130) will be apparent to one of ordinary skill in the art in view of the teachings herein.

Lift assembly (1140) comprises a base portion (1142), a vertical portion (1144), and a pair of protrusions (1146). In the present example, base portion (1142) and vertical portion (1144) are formed as a single homogeneous continuum of material formed in an L shape. Base portion (1142) is sized to at least accommodate insertable component (1150) thereon. Base portion (1142) may further comprise a rim (not shown) extending around the perimeter of base portion (1142), thereby forming a recess into which insertable component (1150) may be inserted. Base portion (1142) may further comprise a cap (not shown) to be coupled to primary housing (1110) when lift assembly (1140) is fully inserted within primary housing (1110). The cap may be constructed in accordance with at least some of the teachings of cap (620), as previously discussed herein, or the cap may have any other suitable configuration as will be apparent to one of ordinary skill in the art in view of the teachings herein. One such feature of cap (620) that may be readily incorporated is to have the present cap frictionally fit to primary housing (1110). Vertical portion (1144) or base portion (1142) may also include an attachment (not shown) for securing insertable component (1150) thereto. This attachment may comprise a mechanical attachment (such as a snap-on fitting, an elastic band, or a latch, etc.) and/or the attachment may comprise an electrical attachment that may also secure the insertable component (1140) (such as a wire harness, a female electrical plug recess, or a male electrical protrusion, etc.). Protrusions (1146) extend outwardly from vertical portion (1144) and are sized and configured to fit within tracks (1130) of primary housing (1110). In the present example, protrusions (1146) are shown as simple rectangular protrusions that slide within tracks (1130). In one alternative, protrusions (1146) may further comprise wheels or ball bearings to further aid the sliding motion within tracks (1130). Lift assembly (1140) may be made from a variety of materials including plastics, polyethylene terephthalate glycol (or PETG), thermoplastic polymer resins, or any other suitable rigid or semi-rigid material for the lift assembly (1140).

To use medical device (1100) having a lift assembly (1140), initially medical device (1100) is sterilized. In one exemplary sterilization technique, medical device (1100) is placed in a field of radiation that can penetrate medical device (1100), such as gamma radiation, x-rays, or high-energy electrons. The radiation may kill bacteria on primary housing (1110), lift assembly (1140), and within insertion recess (1120). Alternatively, medical device (1100) may be sterilized using any other technique known in the art, including but not limited to beta or gamma radiation, ethylene oxide, electron beam sterilization, or steam. Various other suitable sterilization methods that may be provided will be apparent to those of ordinary skill in the art in view of the teachings herein.

Insertable component (1140) is then placed upon base portion (1142). If insertable component (1140) is non-sterile, a non-sterile user, such as a nurse, may place insertable component (1140) on base portion (1142). The sterile user may then slide lift assembly (1140) into insertion recess (1120). If a cap is provided, then the cap may be coupled to primary housing (1110) to seal lift assembly (1140) an insertion component (1150) therein. In one merely exemplary alternative, lift assembly (1140) may further comprise an elastic member (not shown) coupled to primary housing (1110). In this configuration, the elastic member (such as a spring or rubber band) may be in a relaxed position when lift assembly (1140) is fully inserted into insertion recess (1120). When lift assembly (1140) is pulled down to place insertable component (1150) upon base portion (1142), elastic member stretches into a stretched position. Once the force pulling down lift assembly (1140) is removed, the elastic member may automatically return lift assembly (1140) up into insertion recess (1120). With the insertable component (1150) contained therein, the user may then used medical device (1100) for a medical procedure. A seal (not shown) may be positioned between base portion (1142) and primary housing (1110), hermetically sealing insertion recess (112) when lift assembly (1140) is in the closed position.

To remove insertable component (1150) from within insertion recess (1120) of a used medical device (1100), a user may pull lift assembly (1140) downward to expose insertable component (1150) on base portion (1142). The user may then remove insertable component (1150) for recharging, reclamation, and/or reuse; and/or dispose of insertable component (1150) separate from medical device (1100). Thus, in the configuration described, a non-sterile insertable component may be inserted into and used with a medical device while maintaining the sterility of the exterior of the medical device; and may be further protected from body fluids or other fluids that may contact the exterior of the medical device.

The medical device (1200) shown in FIGS. 20A-20B may also be constructed in accordance with at least some of the teachings of medical devices (10, 100), as previously discussed herein, or medical device (1200) may have any other suitable configuration as will be apparent to one of ordinary skill in the art in view of the teachings herein. Medical device (1200) comprises a primary housing (1210) that may be constructed at in accordance with at least some of the teachings of primary housing (1110) described herein. In the present example, primary housing (1210) comprises an insertion recess (1220) configured to accommodate an insertable component (1250). By way of example only, insertable component (1250) may comprise a power source, such as one of the types of batteries previously discussed herein, a plurality of batteries in the form of a battery pack, a control module, a printed circuit board, an ultrasonic transducer, and/or any other insertable component (1250) or combination of components as will be apparent to those of ordinary skill in the art in view of the teachings herein. Primary housing (1210) may be made from a variety of materials including plastics, polyethylene terephthalate glycol (or PETG), thermoplastic polymer resins, or any other suitable rigid or semi-rigid material for the primary housing (1210).

Primary housing (1210) of the present example further comprises a pair of hinge members (1230) and a pair of doors (1240). Hinge members (1230) are mounted to a bottom portion of primary housing (1210). Doors (1240) in the present example are L-shaped doors having a first portion (1242) and a second portion (1244). Doors (1240) are configured to rotate about hinge members (1230). In this configuration, when insertable component (1250) is pressed against the first portion (1242), as shown in FIG. 20A, the L-shaped doors (1240) begin to rotate about hinge members (1230). As the user pushes insertable component (1250) further into insertion recess (1220), second portion (1244) rotates underneath insertable component (1250) to support insertable component (1250). The same user or a different user may at some point switch from pushing directly on insertable component to pushing directly on second portions (1244) of doors (1240). As shown in FIG. 20B, when insertable component (1250) is fully inserted into insertion recess (1220), second portion (1244) of each door (1240) forms a flat planar surface on which insertion component (1240) may rest within medical device (1200). The rotation of doors (1240) may be aided by hinge members (1230) comprising resilient hinges such that when doors (1240) are rotated to an open position, as in FIG. 20A, the resilient hinges are in a stretched state, resiliently urging doors (1240) toward the closed position of FIG. 20B. When the doors (1240) are in a closed position, as in FIG. 20B, the resilient hinges are in a relaxed state.

In yet another merely illustrative alternative, springs (not shown) may be attached at a first end to an interior portion of primary housing (1210) and the other end of each spring may be attached to a portion of the first portion of a corresponding door (1240). As with the resilient hinges, when doors (1240) are rotated to an open position, as in FIG. 20A, the springs are in a stretched state. When doors (1240) are in a closed position, as in FIG. 20B, the springs are in a relaxed state. In another merely illustrative alternative, a single L-shaped door and a single hinge member may be provided instead of a pair of doors. In still another illustrative alternative, a cap may be hingedly attached to primary housing (1210). The cap may be constructed at least partially in accordance with the teachings of cap (720) as described herein. Furthermore, second portions (1244) of doors (1240) may comprise a detent or latching mechanism to further secure doors (1240) in the closed position. Still other suitable features and configurations for doors (1240) and hinge members (1230) will be apparent to one of ordinary skill in the art in view of the teachings herein.

With the insertable component (1250) contained therein, the user may use medical device (1200) for a medical procedure. To remove insertable component (1250) from within insertion recess (1220) of a used medical device (1200), the user rotates doors (1240) to release insertable component (1250). Doors (1240) may further comprise exterior protrusions or recesses (not shown) to aid the user's grasping of doors (1240). Alternatively, a button, slider, or other feature may provide actuation of doors (1240) to rotate doors (1240) to the open position. The user may then remove insertable component (1250) for recharging, reclamation, and/or reuse; or for disposal separate from medical device (1200). Thus, in the configuration described, a non-sterile insertable component may be inserted into and used with a medical device while maintaining the sterility of the exterior of the medical device; and may be further protected from body fluids or other fluids that may contact the exterior of the medical device.

E. Release Mechanisms for Removing Internal Components from Medical Devices

In some settings, it may be desirable to have a releasing feature to prevent an insertable component of a used medical device from touching contaminated portions of the used medical device after use in a procedure. By preventing contamination after releasing the insertable component, the user may be able to reuse the insertable component without having to clean or sterilize the insertable components between uses. By doing so, more medical procedures may be done because of the reduced the time required to prepare the insertable component between uses. Alternatively, if a number of insertable components are rotated in for use with medical devices (e.g., three battery packs per medical device—one being cleaned, one charging, and one in use), eliminating the step of cleaning or resterilization of the insertable components may reduce the number of insertable components needed to have an effective rotation (e.g., just two battery packs—one being charged and one in use). Accordingly, the following release features may be incorporated into a medical device to keep the insertable component clean (e.g., substantially free of body fluids or other fluids on the medical device) while releasing the component from the medical device.

Figure 21A:
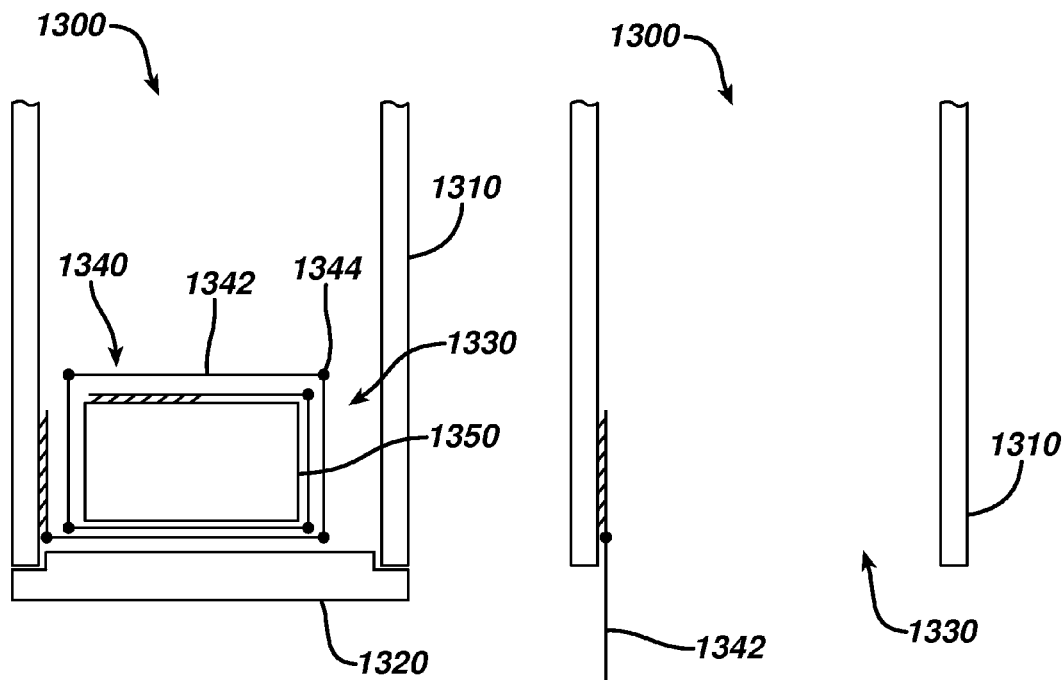
FIG. 21A depicts a side cross-sectional view of a feature for releasing an insertable component from within a medical device, with the protective member shown in an initial position.
Figure 21B:
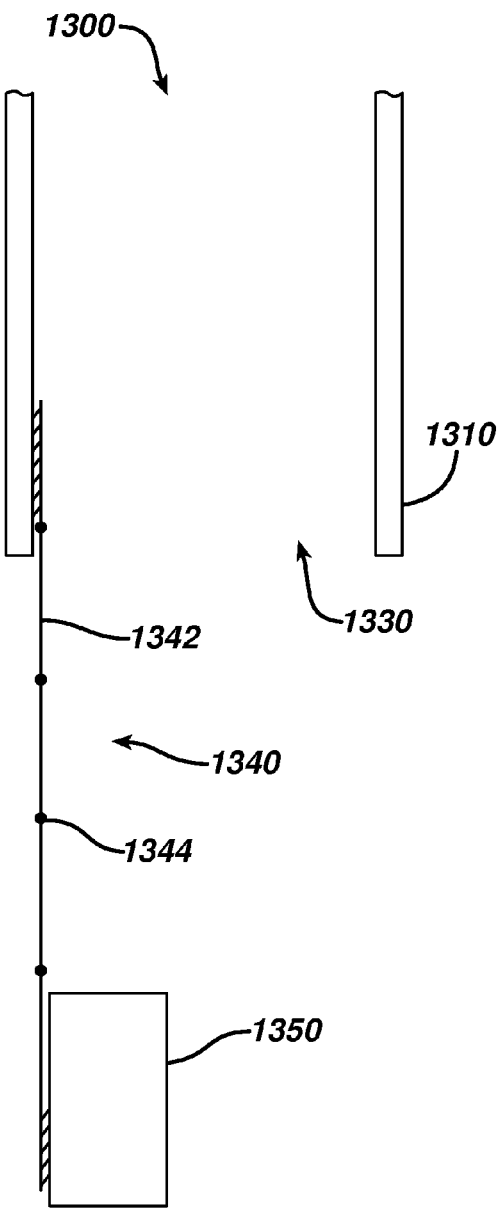
FIG. 21B depicts a side cross-sectional view of the feature shown in 21A, showing the protective member in a released position.

FIGS. 21A-21B depict a medical device (1300) comprising a primary housing (1310) and a cap (1320). Medical device (1300) may be constructed in accordance with at least some of the teachings of medical devices (10, 100), as previously discussed herein, or medical device (1300) may have any other suitable configuration as will be apparent to one of ordinary skill in the art in view of the teachings herein. Primary housing (1310) comprises a protective member (1340) and an insertion recess (1330). Insertions recess (1330) is sized to receive an insertable component (1350). In the present example, insertion recess (1330) is a substantially open cavity within primary housing (1310), though it should be understood that insertion recess (1330) may be sized to accommodate only insertable component (1350) or insertion recess (1330) may have any other suitable size and configuration as will be apparent to one of ordinary skill in the art in view of the teachings herein. Exemplary insertable component (1350) may comprise a power source, such as one of the types of batteries previously discussed herein, a plurality of batteries in the form of a battery pack, a control module, a printed circuit board, an ultrasonic transducer, and/or any other insertable component (1350) or combination of components as will be apparent to those of ordinary skill in the art in view of the teachings herein.

Protective member (1340) of the present example comprises a plurality of segments (1342), though it should be understood that protective member (1340) may alternatively comprise a single piece (such as a length of flexible plastic or rubber) or protective member (1340) may have any other suitable configuration as will be apparent to those of ordinary skill in the art in light of the teachings herein. In the present example, segments (1342) are rigid plate members. However, segments (1342) may have other alternative forms, including, but not limited to, semi-rigid plates, rigid or semi-rigid rod-like links, ladder portions, flexible lengths of plastic or rubber, or any other suitable rigid, semi-rigid, and/or flexible segments or combinations thereof. In the present example, a first segment (1342) is attached at a first end to a portion of primary housing (1310). This attachment may comprise attachment by adhesive, by suitable mechanical coupling, by integral formation with the portion of primary housing (1310), or any other suitable attachment means. A subsequent segment (1342) is coupled to the first segment by a hinge member (1344). Hinge member (1344) of the present example is a butt hinge, though other suitable hinge members may be readily substituted, including piano hinges, barrel hinges, revolute joints, ball and socket joints, or any other suitable hinge member (1344) to allow rotation as will be apparent to one of ordinary skill in the art in view of the teachings herein. A series of successive segment (1342) and hinge member (1344) may be coupled to form protective member (1340). At a second end of protective member (1340) a final segment (1342) is attached to a portion of insertable component (1350). As with the attachment of the first segment (1342), the attachment to insertable component (1350) may comprise attachment by adhesive, by suitable mechanical coupling, by integral formation with the portion of insertion recess (1330), or any other suitable attachment means. Additionally, the final segment (1342) may further comprise a breakaway region (not shown), such as a plurality of perforations, to aid in the detachment of insertable component (1350) from final segment (1342). One merely exemplary alternative attachment may comprise mechanical coupling by an electrical plug. Alternatively, insertable component (1350) may not be attached to the final segment (1342).

Cap (1320) is sized and configured to be secured to primary housing (1310) to retain insertable component (1350) and protective member (1340) within insertion recess (1330). Cap (1320) may be constructed in accordance with at least some of the teachings of cap (300), cover (420), door assembly (520), or cap (620), as previously discussed herein, or cap (1320) may have any other suitable configuration as will be apparent to one of ordinary skill in the art in view of the teachings herein.

In an initial state, the plurality of segments (1342) are folded about the exterior of insertable component (1350) and positioned within insertion recess (1330) of medical device (1300), as shown in FIG. 21A, such that insertable component is wrapped within protective member (1340). Once cap (1320) is decoupled and removed, protective member (1340) unfurls from within insertion recess (1330) due to the force of gravity pulling insertable component (1350) downward. Once all segments (1342) are unfurled, as seen in FIG. 21B, insertable component (1350) may simply drop off from protective member (1340), if not attached, or insertable component (1350) may hang while still attached to the final segment (1342). The user may then detach insertable component (1350) from protective member (1340) for reuse, reclamation, and/or recharging; or for disposal separate from medical device (1300). Thus, protective member (1340) may help prevent insertable component (1350) from touching contaminated portions of used medical device (1300) (e.g., preventing exposure of insertable component (1350) to body fluids on medical device (1300), etc.) while releasing insertable component (1350) from within insertion recess (1330).

In another exemplary configuration, shown in FIGS. 22A-22B, a pair of protective members (1440) may be utilized to facilitate the release of an insertable component (1450). Similar to medical device (1300), medical device (1400) of this example comprises a primary housing (1410) and a cap (1420). Medical device (1400) may be constructed in accordance with at least some of the teachings of medical devices (10, 100), as previously discussed herein, or medical device (1400) may have any other suitable configuration as will be apparent to one of ordinary skill in the art in view of the teachings herein. Primary housing (1410) comprises a pair of protective members (1440), an insertion recess (1430), and a pair of pivots (1412). Insertions recess (1430) is sized to receive an insertable component (1450). In the present example, insertion recess (1430) is a substantially open cavity within primary housing (1410), though it should be understood that insertion recess (1430) may be sized to accommodate only insertable component (1450) or insertion recess (1430) may have any other suitable size and configuration as will be apparent to one of ordinary skill in the art in view of the teachings herein. Exemplary insertable component (1450) may comprise a power source, such as one of the types of batteries previously discussed herein, a plurality of batteries in the form of a battery pack, a control module, a printed circuit board, an ultrasonic transducer, and/or any other insertable component (1450) or combination of components as will be apparent to those of ordinary skill in the art in view of the teachings herein. Pivots (1412) are attached to an interior portion of primary housing (1410). In the present example, pivots (1412) are integrally formed with primary housing (1410), though it should be understood that other suitable attachment for pivots (1412) may be provided as will be apparent to one of ordinary skill in the art in light of the teachings herein.

Protective members (1440) comprise a plurality of segments (1442) and hinge members (1444) that pivotably couple segments (1442) together. In the present example, segments (1442) comprise rigid plate members. However, segments (1442) may have other alternative forms, including, but not limited to, semi-rigid plates, flexible lengths of plastic or rubber, or any other suitable rigid, semi-rigid, and/or flexible segments or combinations thereof. Hinge members (1444) of the present example are butt hinges, though other suitable hinge members may be readily substituted, including piano hinges, barrel hinges, revolute joints or any other suitable hinge member (1444) to allow rotation as will be apparent to one of ordinary skill in the art in view of the teachings herein. Protective members (1440) are rotatably coupled to pivots (1412) at a first end of a first segment (1442). In the present example, first segments (1442) are coupled to pivots (1412) by a pivot pin, though other suitable pivots will be apparent to one of ordinary skill in the art in view of the teachings herein. A subsequent segment (1442) is rotatably coupled to the first segment (1442) by hinge member (1444).

Cap (1420) is sized and configured to be secured to primary housing (1410) to retain insertable component (1450) and protective members (1440) within insertion recess (1430). Cap (1420) may be constructed in accordance with at least some of the teachings of cap (300), cover (420), door assembly (520), or cap (620), as previously discussed herein, or cap (1420) may have any other suitable configuration as will be apparent to one of ordinary skill in the art in view of the teachings herein.

In an initial state, the plurality of segments (1442) are alternately folded upon each other and positioned beneath insertable component (1450) within insertion recess (1430) of medical device (1400), as shown in FIG. 22A. Once cap (1420) is decoupled and removed, the weight of insertable component (1450) causes protective members (1440) to unfold from within insertion recess (1430). As shown in FIG. 22B, this forms a trapdoor-like structure to substantially prevent insertable component (1450) from contacting the contaminated exterior surfaces of medical device (1400) as insertable component (1450) is released. The user then drops insertable component (1450) into a hand or a reclamation bin for reuse, reclamation, and/or recharging; or for disposal separate from medical device (1400). Thus, protective members (1440) may help prevent insertable component (1450) from touching contaminated portions of used medical device (1400) (e.g., preventing exposure of insertable component (1450) to body fluids on medical device (1400), etc.) while releasing insertable component (1450) from within insertion recess (1430).

In yet another exemplary configuration, shown in FIGS. 23A-23B, a protective chute (1540) may be utilized to facilitate the protected release of an insertable component (1550). Similarly to medical device (1300) and medical device (1400), medical device (1500) of this example comprises a primary housing (1510) and a cap (1520). Medical device (1500) may be constructed in accordance with at least some of the teachings of medical devices (10, 100), as previously discussed herein, or medical device (1500) may have any other suitable configuration as will be apparent to one of ordinary skill in the art in view of the teachings herein. Primary housing (1510) comprises an integral chute (1540) and an insertion recess (1530). Insertion recess (1530) is sized to receive an insertable component (1550). In the present example, insertion recess (1530) is a substantially open cavity within primary housing (1510), though it should be understood that insertion recess (1530) may be sized to accommodate only insertable component (1550) or insertion recess (1530) may have any other suitable size and configuration as will be apparent to one of ordinary skill in the art in view of the teachings herein. Exemplary insertable component (1550) may comprise a power source, such as one of the types of batteries previously discussed herein, a plurality of batteries in the form of a battery pack, a control module, a printed circuit board, an ultrasonic transducer, and/or any other insertable component (1550) or combination of components as will be apparent to those of ordinary skill in the art in view of the teachings herein.

Chute (1540) of the present example comprises a length of flexible material (such as plastic film or thin rubber). While chute (1540) has an open bottom in the present example, it should be understood that chute (1540) may alternatively have a closed bottom such that chute (1540) forms a bag. In the present example, a top portion of chute (1540) is attached to a portion of primary housing (1510). This attachment may comprise attachment by adhesive, by suitable mechanical coupling, by integral formation with the portion of primary housing (1510), or any other suitable attachment means. The flexibility of chute (1540) allows chute (1540) to collapse within insertion recess (1530) with insertable component (1550) disposed therein. Cap (1520) is sized and configured to be secured to primary housing (1510) to retain insertable component (1550) and chute (1540) within insertion recess (1530). Cap (1520) may be constructed in accordance with at least some of the teachings of cap (300), cover (420), door assembly (520), or cap (620), as previously discussed herein, or cap (1520) may have any other suitable configuration as will be apparent to one of ordinary skill in the art in view of the teachings herein.

In an initial state, chute (1540) is collapsed and positioned beneath (and/or adjacent to) insertable component (1550) within insertion recess (1530) of medical device (1500), as shown in FIG. 23A. Once cap (1520) is decoupled and removed, chute (1540) unfurls from within insertion recess (1530). As chute (1540) unfurls, insertable component (1550) slides downwardly through chute (1540), as seen in FIG. 23B. The user then drops insertable component (1550) into a hand or a reclamation bin for reuse, reclamation, and/or recharging; or for disposal separate from medical device (1500). If chute (1540) forms a bag structure, the bag may stop insertable component (1550) once insertable component (1550) has reached the bottom of the bag. The user may then detach the bag to transport insertable component (1550). Thus, chute (1540) may help prevent insertable component (1550) from touching contaminated portions of used medical device (1500) (e.g., preventing exposure of insertable component (1550) to body fluids on medical device (1500), etc.) while releasing insertable component (1550) from within insertion recess (1530).

While various configurations for protective members have been described, it should be understood that some or all of portions of protective members (1340, 1440, 1540) may readily be interchangeable or used in combination as will be apparent to one of ordinary skill in the art in view of the teachings herein. Moreover, protective members (1340, 1440, 1540) may be readily incorporated into medical devices (200, 500, 600, 700, 800, 950, 1000, 1200) or any other suitable medical device as will be apparent to one of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for maintaining sterility of a medical device while providing for insertion of an insertable component into the medical device, the apparatus comprising:
    (a) a medical device, wherein the medical device comprises:
        (i) a housing, wherein the housing is sized to contain at least part of an insertable component,
        (ii) an active feature selectively activated or controlled by an insertable component contained in the housing,
        (iii) a cap, wherein the cap is sized and configured to couple to and seal the housing, wherein the cap is movable from an open position to a closed position, and
        (iv) a hinge member, wherein the hinge member pivotably couples the housing with the cap; and
    (b) a container, wherein the container comprises:
        (i) a device recess, wherein the device recess is sized and configured to contain the housing,
        (ii) a cap recess, wherein the cap recess is sized and configured to contain the cap when the cap is in the open position, and
        (iii) a first container cover, wherein the first container cover is sized and configured to removably cover both the device recess and the cap recess;
        wherein the first container cover is configured to cooperate with the container in a manner sufficient to maintain sterility of the medical device within the container.

2. The apparatus of claim 1, wherein the hinge member comprises a resilient hinge resiliently biased to urge the cap from the open position to the closed position.

3. The apparatus of claim 2, wherein the container further comprises a second container cover, wherein the second container cover is sized and configured to removably cover to the cap recess.

4. The apparatus of claim 1, wherein the medical device further comprises an elastic member, wherein the elastic member has a first end and a second end, wherein the first end of the elastic member is attached to a portion of the housing, and wherein the second end of the elastic member is attached to a portion of the cap.

5. The apparatus of claim 4, wherein the housing further comprises a retention feature, wherein the retention feature is configured to retain an insertable component within the housing when an insertable component is inserted therein.

6. The apparatus of claim 5, wherein the retention feature comprises a spring and a latch member.

7. The apparatus of claim 4, wherein the container further comprises a second container cover, wherein the second container cover is sized and configured to removably cover the cap recess.

8. The apparatus of claim 7, wherein the elastic member is made of a material selected from a group consisting of silicone rubber, ethylene propylene diene rubber (EPDM), nitrile rubber, styrene-butadiene rubber, butyl rubber, chloroprene, polychloroprene, polybutadiene rubber, or isoprene rubber.

9. The apparatus of claim 1, wherein the first container cover has a first end and a second end, wherein the first container cover further comprises a pull tab having a first and second end, wherein the first end of the pull tab is attached to the second end of the first container cover, wherein the second end of the pull tab is attached to a portion of the cap.

10. The apparatus of claim 1, wherein the container further comprises a second container cover, wherein the second container cover is sized and configured to removably attach to the cap recess, wherein the second container cover has a first end and a second end, wherein the second container cover further comprises a pull tab having a first and second end, wherein the first end of the pull tab is attached to the second end of the second container cover, wherein the second end of the pull tab is attached to a portion of the cap.

11. The apparatus of claim 10, wherein the pull tab is adhesively attached to both the second container cover and the cap.

12. The apparatus of claim 1, wherein the cap comprises a resilient member, wherein the housing comprises a recess sized and configured to receive the resilient member, and wherein the cap is detachably attached to the housing when the resilient member is inserted into the recess.

13. The apparatus of claim 1, wherein the insertable component comprises a power source.

14. The apparatus of claim 1, wherein the first container cover is adhesively attached to the container.

15. The apparatus of claim 1, wherein the container comprises a blister tray, wherein the blister tray is formed of a single homogeneous continuum of material.

* * * * *